(12) United States Patent
Drauz et al.

(10) Patent No.: US 6,800,464 B2
(45) Date of Patent: Oct. 5, 2004

(54) ARTHROBACTER D-CARBAMOYLASE AND METHODS OF PREPARING ENANTIOMERICALLY ENRICHED D-AMINO ACIDS

(75) Inventors: Karlheinz Drauz, Freigericht (DE); Oliver May, Frankfurt (DE); Andreas Bommarius, Atlanta, GA (US); Christoph Syldatk, Stuttgart (DE); Josef Altenbuchner, Nufringen (DE); Markus Werner, Weinsberg (DE); Martin Siemann-Herzberg, Wildberg (DE)

(73) Assignee: Degussa AG, Duesseldorf (DE)

( * ) Notice: Subject to any disclaimer, the term of this patent is extended or adjusted under 35 U.S.C. 154(b) by 56 days.

(21) Appl. No.: 10/105,294

(22) Filed: Mar. 26, 2002

(65) Prior Publication Data

US 2003/0143244 A1 Jul. 31, 2003

(30) Foreign Application Priority Data

Mar. 26, 2001 (DE) ........................................ 101 14 999

(51) Int. Cl.$^7$ ............................................... C12P 13/04
(52) U.S. Cl. ...................... 435/106; 435/183; 435/196; 435/252.3; 435/320.1; 536/23.2
(58) Field of Search ................................ 435/106, 183, 435/196, 252.3, 320.1; 536/23.2

(56) References Cited

FOREIGN PATENT DOCUMENTS

| WO | WO 94/00577 | | 1/1994 |
|---|---|---|---|
| WO | WO94/00577 | * | 1/1994 |

OTHER PUBLICATIONS

Attwood et al. Which craft is best in bioinformatics? Comput. Chem. 2001, vol. 25(4), pp. 329□339.*
Ponting, C.P. Issues in predicting protein function from sequence. Brief. Bioinform. Mar. 2001, vol. 2(1), pp. 19□29.*
Nelson et al. Accession AAQ54838. Jul. 7, 1994.*
D.–M. Kim, et al., Biotechnology Letters, vol. 16, No. 1, pp. 11–16, "Enhancement of Operational Stability of Immobilized Whole Cell D–Hydantoinase", Jan. 1994.
A. Louwrier, et al., Enzyme and Microbial Technology, vol. 19, pp. 562–571, "The Purification and Characterization of a Novel D(—)–Specific Carbamoylase Enzyme from an Agrobacterium sp.", Dec. 1996.
C. Syldatk, et al., Habilitationsarbeit, pp. 131–175, "Microbial and Enzymatic Production of L–Amino Acids from DL–5–Monosubstituted Hydantoins", 1990.

H. Nanba, et al., Biosci. Biotechnol. Biochem., vol. 62, No. 5, pp. 875–881, "Isolation of Agrobacterium sp. Strain KNK712 that Produces N–Carbamyl–D–Amino Acid Amidohydrolase, Cloning of the Gene for this Enzyme, and Properties of the Enzyme", 1998.
Syldatk, et al., Editors: Drauz & Waldmann, 1st and 2nd Edition, pp. 409–433 and 486–495, "Enzyme Catalysis in Organic Synthesis".
A. Moeller, et al., Enzyme and Microbial Technology, vol. 10, No. 10, pp. 618–625, XP–008007367, "Stereo–and Substrate–Specificity of a D–Hydantoinase and a D–N–Carbamyl–Amino Acid Amidohydrolase of *Arthrobacter Crystallopoietes* AM 2",, Jul. 1988.
R. Grifantini, et al., Microbiology, vol.144, No. 4, pp. 947–954, XP–002154848, "Efficient Conversion of 5–Substituted Hydantoins to D–α–Amino Acids Using Recombinant *Escherichia coli* Strains", Apr. 1998.
Y. Ikenaka, et al., Bioscience, Biotechnology, and Biochemistry, vol. 62, No. 5, pp. 882–886, XP–001074193, "Screening, Characterization, and Cloning of the Gene for N–Carbamyl–D–Amino Acid Amidohydrolase from Thermotolerant Soil Bacteria", May 1998.
A. Buson, et al., FEMS Microbiology Letters, vol. 145, pp. 55–62, XP–002934364, "Identification, Sequencing and Mutagenesis of the Gene for a D–Carbamoylase from *Agrobacterium Radiobacter*", 1996.
H. Nanba, et al., Bioscience, Biotechnology, and Biochemistry, vol. 62, No. 5, pp. 875–881, XP–001074192, "Isolation of Agrobacterium sp. Strain KNK712 that Produces N–Carbamyl–D–Amino Acid Amidohydrolase, Cloning of the Gene for this Enzyme and Properties of the Enzyme", May 1998.
C. Syldatk, et al., Biocatalytic Production of Amino Acids and Derivatives, pp. 75–128, XP–000991524, "Microbial and Enzymatic Production of D–Amino Acids from DL–5–Monosubstituted Hydantoins", 1992.

* cited by examiner

*Primary Examiner*—Ponnathapu Achutamurthy
*Assistant Examiner*—Christian L. Fronda
(74) *Attorney, Agent, or Firm*—Oblon, Spivak, McClelland, Maier & Neustadt, P.C.

(57) ABSTRACT

The present invention relates to a new D-carbamoylase and the gene sequences which code for this from the organism *Arthrobacter crystallopoietes* DSM 20117. Plasmids, vectors, microorganisms, particular primers and specific possible uses of the enzymes according to the invention are also mentioned. The invention moreover describes a new process for the discovery of enzymes which can be employed in a process for the preparation of D-amino acids starting from 5'-substituted hydantoins.

28 Claims, 10 Drawing Sheets

Fig. 10 (Equation 1)
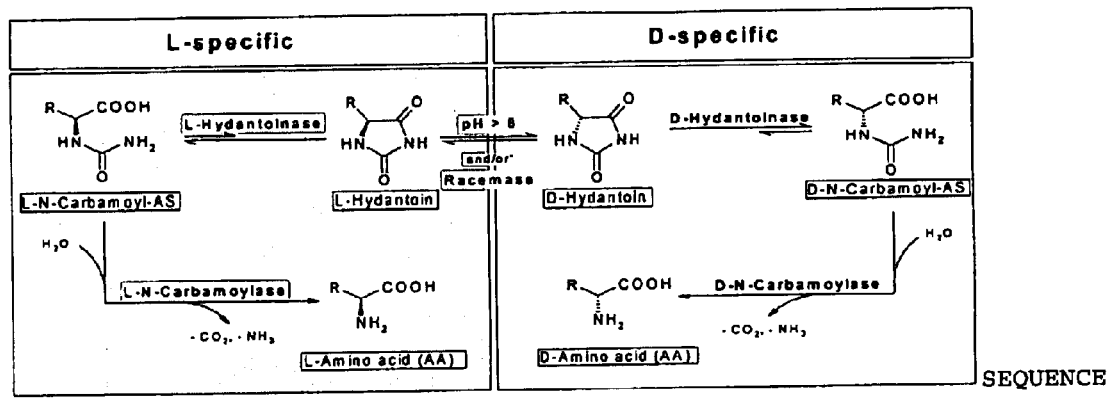
PROTOCOL SEQUENCE

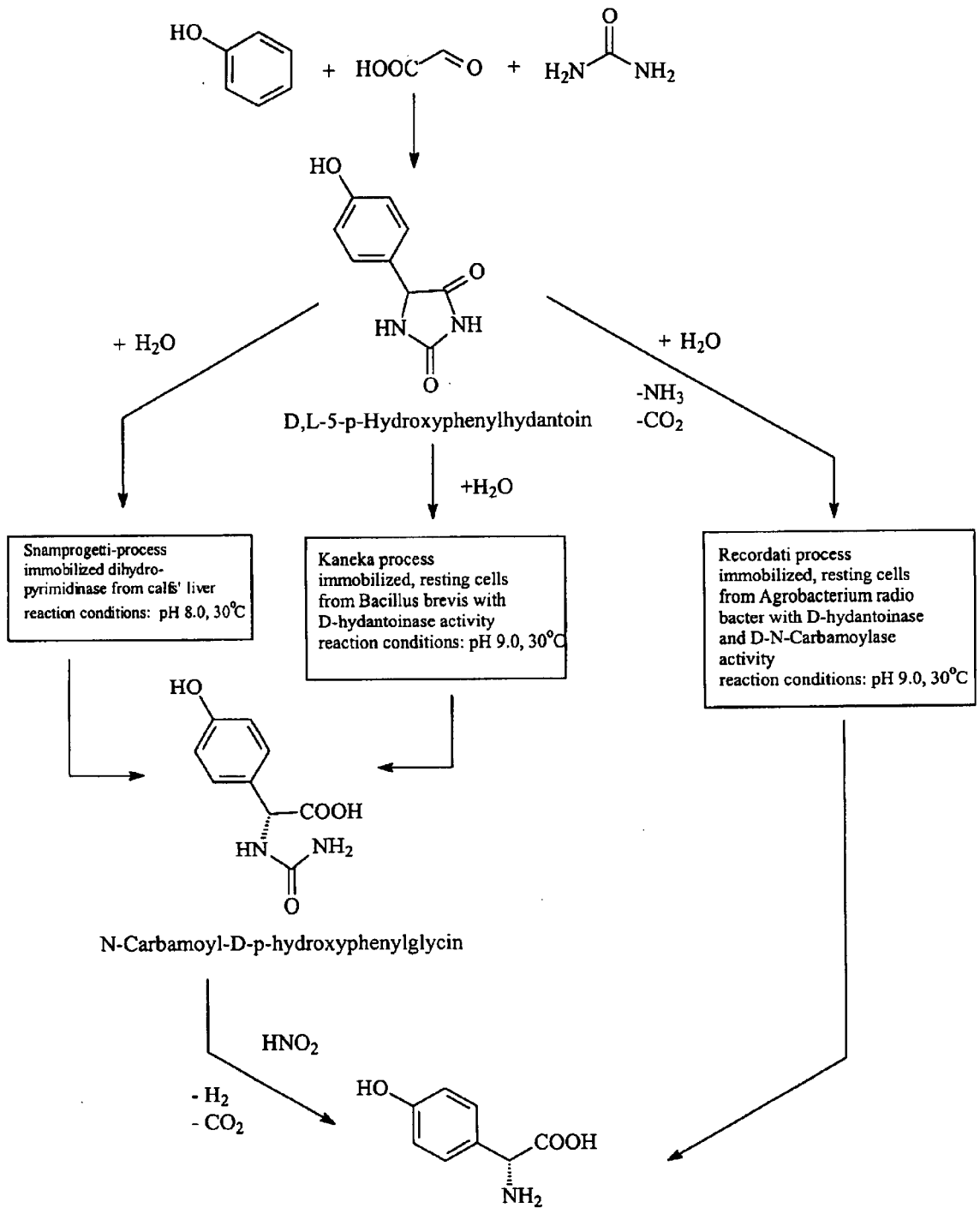
Fig. 11 (Equation 2)

ARTHROBACTER D-CARBAMOYLASE AND METHODS OF PREPARING ENANTIOMERICALLY ENRICHED D-AMINO ACIDS

CROSS-REFERENCE TO RELATED APPLICATIONS

This application claims priority to German priority document 101 14 999.9, filed Mar. 26, 2001, that is hereby incorporated by reference.

REFERENCE TO SEQUENCE LISTING

The computer-readable sequence(s) on the attached compact disk are hereby incorporated by reference.

BACKGROUND OF THE INVENTION

1. Field of the Invention

D-carbamoylases and polypeptides having D-carbamoylase activity, especially those from Arthrobacter. D-carbamoylases that are more economical, efficient and conveniently used in commercial and industrial processes, such as those with superior activity or stability. Nucleic acids, vectors and host cells encoding or expressing these D-carbamoylases. Methods for making an enantiomerically enriched or purified amino acid using such a D-carbamoylase and methods for identifying and isolating a gene, gene cluster or operon encoding a D-carbamoylase.

2. Description of Related Art

Carbamoylases are enzymes which are capable of converting N-carbamoylamino acids stereoselectively into the L- or D-amino acid, while retaining the enantiomeric carbamoylamino acid, see equation 1 in FIG. 10.

Racemic N-carbamoylamino acids can preferably be obtained quite easily from hydantoins by means of hydantoinases or by reaction of amino acids with KOCN, and for this reason such processes are used on an industrial scale for the preparation of enantiomerically concentrated amino acids (Drauz K, Kottenhahn M, Makryaleas K, Klenk H, Bernd M, Angew Chem, (1991). Chemoenzymatic synthesis of D-ω-ureidoaminoacids, 103, 704–706; See Equation 2 in FIG. 11.

D-Carbamoylases are known in the literature (Syldatk et al. in "Enzymatic Catalysis in Organic Synthesis", eds.: Drauz, Waldmann, VCH, $1^{st}$ and $2^{nd}$ Ed.), but these mostly do not work very efficiently or are unstable (Syldatk C, M üller R, Pietzsch M, Wagner F (1992). Biocatalytic production of amino acids & derivatives; eds.: Rozzell D, Wagner F, Hanser Publishers, Munich; 129–176; Louwrier A, Knowles C. J. (1996). The purification and characterization of a novel D-specific carbamoylase enzyme from Agrobacterium sp. Enzyme Microb Technol. 19; 562–571; Nanba H, Ikenaka Y, Yamada Y, Yajima K, Takano M Takahashi S (1998). Isolation of Agrobacterium sp. strain KNK712 that produces N-carbamyl-D-amino acid amidohydrolase, cloning of the gene for this enzyme, and properties of the enzyme. Biosci. Biotechnol. Biochem. 62 (5) 875–881; Kim D. M., Kim G. J., Kim H. S. (1994). Biotechnol Lett, (16) 11–16). Accordingly, there is a need for further improved carbamoylases, such as those with improved stability or activity.

BRIEF SUMMARY OF THE INVENTION

The present invention encompasses D-carbamoylases and polypeptides having D-carbamoylase activity, especially those from Arthrobacter. These D-carbamoylases provide a more economical, efficient and conveniently usable D-carbamoylase, for instance, a D-carbamoylase with superior stability or activity. The invention also encompasses nucleic acids encoding such a D-carbamoylases or polypeptide having a D-carbamoylase activity, as well as plasmids and microorganisms encompassing such a nucleic acid sequence. Methods for making an enantiomerically enriched or purified amino acid using such a D-carbamoylase and methods for identifying and isolating a gene, gene cluster or operon encoding a D-carbamoylase are also described.

The use of an enzymatic process for the synthesis of an organic compound, such as a D-amino acid is advantageous, particularly for large scale industrial process, since such a process often provides a superior product yield and improved reactant or product selectivity compared to a conventional chemical process. In nature, enzymatic process are of decisive importance, for instance, in the biosynthesis of proteins such as albumins. Accordingly, an efficient and convenient enzymatic process for producing enantiomerically concentrated amino acids is a preferred target of the present invention. Enantiomerically concentrated amino acids are important products for the synthesis of bioactive compounds or for the production of other products, such as those used for parenteral feeding.

BRIEF DESCRIPTION OF THE DRAWINGS

FIG. 10 depicts reaction Equation 1.

FIG. 11 depicts reaction Equation 2.

DETAILED DESCRIPTION OF THE INVENTION

Figure 1:
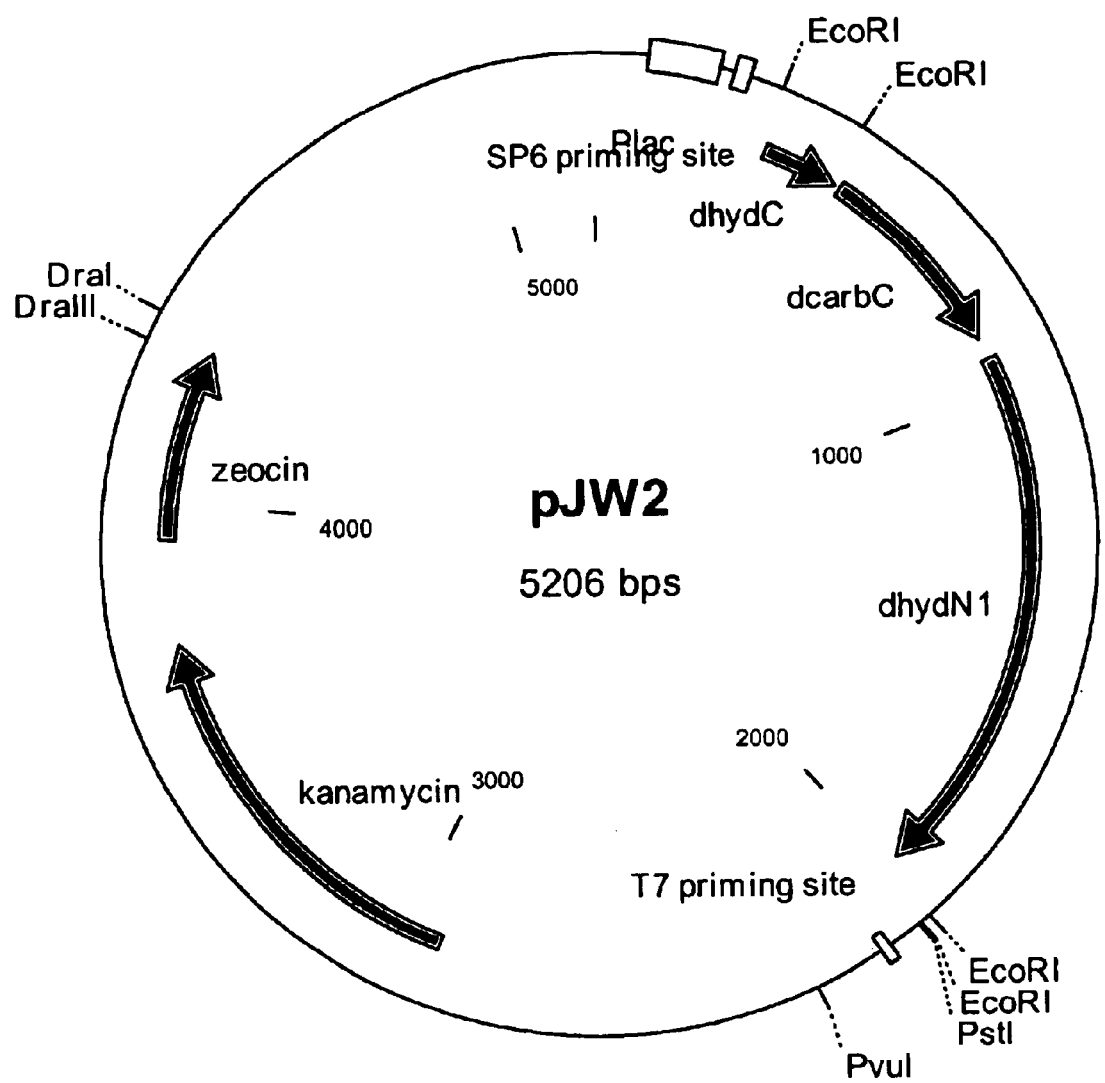
FIG. 1 depicts plasmid pJW2.

One embodiment of the invention relates to gene sequences, such as that of SEQ ID NO: 1 or to degenerate sequences that encode the polypeptide of SEQ ID NO: 2, as well as those that encoded structurally and functionally related D-carbamoylases or polypeptides having D-carbamoylase activity.

Similarly, another embodiment of the invention relates to plasmids or vectors containing the gene sequences according to the invention. In principle, one with skill in the art could select a suitable plasmid or vector into which a nucleic acid sequence of the present invention could be inserted or expressed. Such plasmids and vectors are described in Studier et al., Methods Enzymol. 1990, 185, 61–69 or the brochures of Novagen, Promega, New England Biolabs, Clontech or Gibco BRL. Further preferred plasmids and vectors can be found in: DNA cloning: a practical approach. volume I–III, edited by D. M. Glover, IRL Press Ltd., Oxford, Washington DC, 1985, 1987; Denhardt, D. T. and Colasanti, J.: A surey of vectors for regulating expression of cloned DNA in *E. coli*. In: Rodriguez, R. L. and Denhardt, D. T (eds), Vectors, Butterworth, Stoneham, MA, 1987, pp179–204; Gene expression technology. In: Goeddel, D. V. (eds), Methods in Enzymology, volume 185, Academic Press, Inc., San Diego, 1990; Sambrook, J., Fritsch, E. F. and Maniatis, T. 1989. Molecular cloning: a laboratory manual, 2$^{nd}$ ed. Cold Spring Harbor Laboratory Press, Cold Spring Harbor, N.Y.

Preferred host organisms for the cloning and expression of plasmids or vectors encompassing a gene construct according to the present invention are: pKK-177-3H (Roche Biochemicals), pBTac (Roche Biochemicals), pKK-233 (Stratagene) or pET (Novagen). With the exception of the TOPO series, which has an integrated kanamycin resistance, such other plasmids should contain a β-lactamase for ampicillin resistance. Particularly preferred plasmids are the following:

| Name | Properties | Primer involved |
|---|---|---|
| pJW2 (FIG. 1) | pCRTOPOB1untII with amplicon from IPCR 1 | IPCR1+/− |
| pRW (FIG. 2) | pCRTOPOB1untII with amplicon from IPCR 2 | IPCR5+/5− | invention by means of all types of PCR. These also include the sense and antisense primers which code for the corresponding amino acid sequence.

Suitable primers can in principle be obtained by processes known to the expert. The discovery of the primers according to the invention is undertaken by comparison with known DNA sequences or by transcribing the amino acid sequences under consideration into the codon of the organism in question (e.g. for Streptomyces: Wright et al., Gene 1992, 113, 55–65). Common features in the amino acid sequence of proteins of so-called super-families is also of use for this (Firestine et al., Chemistry & Biology 1996, 3, 779–783). Further information in this respect can be found in Oligonucleotide synthesis: a practical approach, edited by M. J. Gait, IRL Press Ltd, Oxford Washington DC, 1984; PCR Protocols: A guide to methods and applications, edited by M. A. Innis, D. H. Gelfound, J. J. Sninsky and T. J. White. Academic Press, Inc., San Diego, 1990. The following primers are exceptionally preferred:

| Name | Sequence | SEQ ID NO: |
|---|---|---|
| *Primers for IPCR:* | | |
| IPCR1+ | 5'-GAT GTT CAC GCA CCT TCT TTC ACT TC -3' | 3 |
| IPCR1− | 5'-GGT GTT GTA GCC CAG GAC GAC GAG C -3' | 4 |
| IPCR5+ | 5'-GAG GGC GAT GAA GTC GTC GTT GTG AA -3' | 5 |
| IPCR5− | 5'-GTT CTG GTA TGC CCC TGC CTG AAG T -3' | 6 |
| *Primers for cloning structural genes:* | | |
| K_DCn2 | 5'-AAC ATA TGG CGA AAA ACT TGA TGC TC-3' | 7 |
| K_DCc2 | 5'-AAG GAT CCG TCA TTC ACG TTG AAC GG -3' | 8 |
| K_DCc3 | 5'-AAG GAT CCT TAG TCA TTC ACG TTG AAC GG-3' | 9 |

The invention likewise relates to microorganisms containing the gene sequences according to the invention. Any microorganism into which the gene sequence may be cloned and expressed may be used for obtaining the recombinant enzyme. The processes for this are well-known to the expert (Sambrook et al. 1989, Molecular cloning: A Laboratory Manual, 2nd Edition, Cold Spring Harbor Laboratory Press, Balbas P & Bolivar F. 1990, Design and construction of expression plasmid vectors in *E. col*, Methods Enzymology 185, 14–37). Microorganisms which can be used are, in principle, any organism available to the expert for this purpose. *E. coli* strains are preferably used for this purpose. The following are very particularly preferred: *E. coli* NM 522, JM109, JM105, RR1, DH5α, TOP 10⁻or HB101. Plasmids with which the gene construct containing the gene sequence according to the invention is preferably cloned into the host organism are mentioned above.

A following aspect of the invention relates to primers for the preparation of the gene sequences according to the Another important object of the invention is the provision of a D-carbamoylase or a polypeptide having D-carbamoylase activity for use in a process for preparing an amino acid. For instance, a D-carbamoylase according to the present invention may be used in methods of preparing an enantiomerically enriched or purified D-amino acid, including an amino acid with a non-natural radical. For instance, it may be used in the production of a hydrophobic amino acid, such as alanine, cysteine, histidine, isoleucine, leucine, lysine, methionine, phenylalanine, threonine, tryptophan, tyrosine, or valine; a positively charged amino acid, such as arginine, histidine or lysine; a negatively charged amino acid, such as aspartate or glutamine; an aromatic amino acid, such as histidine, phenylalanine, tryptophan or tyrosine; or for the production of an aliphatic amino acid such as isoleucine, leucine or valine.

Specifically, the D-Carbamoylase from Arthrobacter crystallopoietes DSM 20117 (SEQ ID NO: 2) may be advantageously employed in a process for the preparation of an amino acid. Such processes are known in principle to the expert (WO0058449, WO0008374, DE100050123.0 or DE10050124.9 and the literature cited therein). Either the native enzyme or an enzyme advantageously prepared by a recombinant process may be used for the preparation of an amino acid. The preparation of the rec-enzymes according to the invention may be carried out by genetic engineering processes known to the expert (Sambrook J, Fritsch E F, Maniatis T (1989). Molecular Cloning. Cold Spring Harbour Laboratory Press; Vectors: A Survey of Molecular Cloning Vectors and Their Uses. R. L. Rodriguez & D. T. Denhardt, eds: 205–225). In respect of the general procedures (PCR and fusion PCR, inverse PCR, cloning, expression etc.) reference is made to the following literature and that cited there: Riley J. Butler R, Finniear R, Jenner D, Powell S, Anand R, Smith J C, Markham A F (1990). A novel, rapid method for the isolation of terminal sequences from yeast artificial chromosome (YAC) clones. Nucl Acids Res. 18, 8186; Triglia T, Peterson M. G., Kemp D. J. (1988). A procedure for in vitro amplification of DNA segments that lie outside the boundaries of known sequences. Nucleic Acids Res. 16, 8186; Sambrook J, Fritsch E F, Maniatis T (1989). Molecular Cloning. Cold Spring Harbour Laboratory Press; Vectors: A Survey of Molecular Cloning Vectors and Their Uses. R. L. Rodriguez & D. T. Denhardt, II).

Further aspects of the invention relate to the uses of the D-carbamoylase according to the invention. In principle, these can be employed in all processes possible to the expert, e.g. for the preparation of enantiomerically concentrated amino acids, which can preferably be employed in parenteral feeding or animal nutrition. However, the optically concentrated amino acids prepared in this way are furthermore preferably used for the synthesis of bioactive compounds.

Processes for the preparation of enantiomerically concentrated amino acids are, inter alia, those processes which are mentioned in WO0058449, WO0008374, DE100050123.0 or DE10050124.9 and the literature cited there. These can be carried out completely analogously with the D-carbamoylase of the present invention.

The processes just mentioned for the preparation of amino acids are preferably carried out starting from hydantoins in the system hydantoinase/D-carbamoylase, optionally in the presence of a hydantoin racemase or an enzyme which is capable of racemization of carbamoylamino acids (WO0058449, WO0008374). The process according to the invention is particularly preferably carried out in an enzyme membrane reactor (DE 199 10 691.6).

The carbamoylase according to the invention can be used in a further use for the preparation of enzymes modified by genetic engineering. Such processes are known in principle to the expert (Eigen M. and Gardinger W. (1984) Evolutionary molecular engineering based on RNA replication. Pure & Appl. Chem. 56(8), 967–978; Chen & Arnold (1991) Enzyme engineering for nonaqueous solvents: random mutagenesis to enhance activity of subtilisin E in polar organic media. Bio/Technology 9, 1073–1077; Horwitz, M. And L. Loeb (1986) "Promoters Selected From Random DNA-Sequences" Proceedings Of The National Academy Of Sciences Of The United States Of America 83(19): 7405–7409; Dube, D. And L. Loeb (1989) "Mutants Generated By The Insertion Of Random Oligonucleotides Into The Active-Site Of The Beta-Lactamase Gene" Biochemistry 28(14): 5703–5707; Stemmer PC (1994). Rapid evolution of a protein in vitro by DNA shuffling. Nature. 370; 389–391 and Stemmer PC (1994) DNA shuffling by random fragmentation and reassembly: In vitro recombination for molecular evolution. Proc Natl Acad Sci USA. 91; 10747-10751).

The carbamoylase of the present invention may encompass such engineered or modified enzymes, for instance, a D-carbamoylase having at least 70%, preferably at least 80%, more preferably at least 90%, 95% or 99% homology or similarity with the carbamoylase encoded by SEQ ID NO: 1. Homology, sequence similarity or sequence identity of nucleotide or amino acid sequences may be determined conventionally by using known software or computer programs such as the BestFit or Gap pairwise comparison programs (GCG Wisconsin Package, Genetics Computer Group, 575 Science Drive, Madison, Wisconsin 53711). BestFit uses the local homology algorithm of Smith and Waterman, Advances in Applied Mathematics 2: 482–489 (1981), to find the best segment of identity or similarity between two sequences. Gap performs global alignments: all of one sequence with all of another similar sequence using the method of Needleman and Wunsch, J. Mol. Biol. 48:443–453 (1970). When using a sequence alignment program such as BestFit, to determine the degree of sequence homology, similarity or identity, the default setting may be used, or an appropriate scoring matrix may be selected to optimize identity, similarity or homology scores. Similarly, when using a program such as BestFit to determine sequence identity, similarity or homology between two different amino acid sequences, the default settings may be used, or an appropriate scoring matrix, such as blosum45 or blosum80, may be selected to optimize identity, similarity or homology scores. Alternatively, the carbamoylase of the present invention may be encoded by a nucleic acid sequence which hybridize sunder stringent conditions with the nucleic acid sequence of SEQ ID NO: 1. Stringent conditions are known to those in the art and may include, for example, hybridization followed by washing in 5× SSC at a temperature ranging from 50° to 68° C.

The D-carbamoylases or other enzymes of the present invention may be thus engineered and selected for their activity or stability under different conditions, such as at different pH's or at different temperatures. Other selection criteria may also be employed such as substrate selectivity, convenience of preparation, usage or storage, or for superior efficiency or activity in a particular chemical process.

The strain *Arthrobacter crystallopoietes* DSM 20117 was investigated in respect to the conversion of hydantoin derivatives in the doctoral thesis of A. Marin (Stuttgart, 1997). It was possible to purify D-hydantoinase homogenously from it and to determine the first 30 amino acids of the N terminus of D-hydantoinase.

However, a chromatographic purification of a D-carbamoylase failed since this is evidently an extremely unstable enzyme. Cloning of the D-carbamoylase according to the invention was rendered possible, however, via the roundabout route of cloning of D-hydantoinase. By using the degenerated PCR and inverse PCR, which confirmed the existence of a hyu gene cluster, the gene sequences of the D-carbamoylase structural gene from DSM 20117 was decoded. The recombinant production of the D-carbamoylase in *Escherichia coli* was then made possible, and the gene product was characterized in respect to its function as a novel D-carbamoylase.

The enzyme mentioned, optionally in combination with further enzymes (e.g. hydantoinase/racemase see WO0058449, WO0008374) can be used in the free form as a homogeneously purified compounds or as an enzyme prepared by a recombinant process. It can also be employed as a constituent of an intact (guest) organism or in combination with the broken-down cell mass of the particular host organisms which has been purified to any desired extent. The use of such enzymes in an immobilized form is also possible (Bhavender P. Sharma, Lorraine F. Bailey and Ralph A. Messing, "Immobilisierte Biomaterialiern—Techniken und Anwendungen {Immobilized Biomaterials—Techniques and Uses}", Angew. Chem. 1982, 94, 836–852). The immobilization is advantageously carried out by lyophilization (Dordick et al. J. Am. Chem. Soc. 194, 116, 5009–5010; Okahata et al. Tetrahedron Lett. 1997, 38, 1971–1974; Adlercreutz et al. Biocatalysis 1992, 6, 291–305). Lyophilization in the presence of surface-active substances, such as Aerosol OT or polyvinylpyrrolidone or polyethylene glycol (PEG) or Brij 52 (diethylene glycol mono-cetyl ether) is very particularly preferred (Goto et al. Biotechnol. Techniques 1997, 11, 375–378). Use as CLECs is also conceivable (Vaghjiani et al., Biocat. Biotransform. 2000, 18, 157 et seq.).

As the results of the conversions of N-carbamoylamino acids with D-carbamoylase show, a number of various substrates can be successfully converted (see Table 5 which follows). The activity of the enzyme according to the invention in respect of alanine is of prominence here. The D-carbamoylase from *Arthrobacter crystallopoietes DSM 20117* is identical to a maximum of 53% to the D-carbamoylases described hitherto.

Another embodiment of the present invention is a product or composition comprising a D-amino acid produced using a D-carbamoylase or polypeptide having a D-carbamoylase activity of the present invention. The amino acids produced by the processes of the present invention may also be further modified into forms such salts or amino acid complexes, into a form that converts into an amino acid once ingested, or into a form that is more stable or easily metabolized. For instance, they may be esterified, converted into the corresponding alcohol, or acetylated.

The amino acids produced by the inventive processes may be used in other synthetic process such as synthesis of peptides, such as dipeptides or tripeptides, including flavor enhancers or modifiers and sweetening agents, biological response inhibitors or enhancers, or into polypeptides. As many naturally-occuring enzymes acting on amino acids or peptides have asymmetric binding sites, D-amino acids may be incorporated into products to provide resistance to degradation by such enzymes.

D-amino acids may also be incorporated into foods, dietetic products, nutritional products or supplements or into cosmetics, including moisturizing agents, skin care creams, lotions, or shampoos. D-amino acids may be into polymers or polyaminoacids or used in products such as liquid crystals, artificial leather, or in medical products, such as artificial skin or wound dressings. D-amino acids may also be used as intermediate products in various chemical processes, such as in the synthesis of drugs or agricultural chemicals, for instance, D-valine may be used in the synthesis of pyrethroids. They can be also formulated into products, such as buffers, bacteriostatic agents, or surfactants. Other uses of D-amino acids are known to those of skill in the art and are also incorporated by reference to the Kirk-Othmer Encyclopedia of Chemical Technology, $4^{th}$ edition, vol. 2, pages 504–571.

In another embodiment, the invention relates to a process for the discovery of a chromosomally coded gene which codes for an enzyme which can participate in a process for the preparation of D-amino acids from 5'-substituted hydantoins, wherein a) chromosomal DNA of an organisms which is capable of producing D-amino acids from 5'-substituted hydantoins is divided into fragments, b) these are then cloned into plasmids, c) the plasmids are hybridized with oligonucleotides which contain the sequence information of a hydantoinase or a D-carbamoylase d) starting from the successful hydantoinase hybridization, D-carbamoylase sequences, or in the case of successful D-carbamoylase hybridization hydantoinase sequences are identified in the same plasmid.

The correspondingly coded enzymes can be prepared by processes known to the expert by means of the sequences identified in this way. The enzymes according to the invention described here are preferably obtained by this strategy.

The process described can be used successfully in all cases in which on the one hand native enzymes can be isolated only with difficulty or not at all by purification, and on the other hand the organization of enzymes participating in the reaction in question is present in associated form, e.g. on an operon. The organization of D-hydantoinases and D-carbamoylases in an operon has already been described, inter alia, in the doctoral thesis of Martin Hils (Stuttgart, 1998). The operons identified for Agrobacterium sp. IP I-671 and *Agrobacterium radiobacter* NRRL B11291 do not originate here from chromosomal DNA, but are located on naturally occurring plasmids of the particular organisms which are often difficult to isolate. The same also applies to Pseudomonas sp. NS671, in which the enzymes for an L-selective hydantoin breakdown pathway are coded on the naturally occurring plasmid thereof (Watabe, K.; Ishiwaka, T.; Nakamura, H. 1992, Cloning and sequencing of the genes involved in the conversion of 5-substituted hydantoins to the corresponding L-amino acids from the native plasmid of Pseudomonas sp. NS671, J.Bacteriol. 174:962–969). The use of chromosomal DNA described for discovering such D-selective enzymes is therefore not obvious. Rather, plasmid DNA of the corresponding organisms would preferably be used as the starting material for the cloning of a D-selective hydantoinase-carbamoylase operon. It is therefore surprising that starting from sequence information for a D-hydantoinase it was possible to find a chromosomal gene encoding a D-carbamoylase. This knowledge can now be used industrially so that the sequence information of a hydantoinase, or the activity thereof, can be used for isolation of a D-carbamoylase from chromosomal DNA which is easy to isolate (including from soil samples). The knowledge of a D-carbamoylase sequence or the activity thereof can also be used to isolate a D-hydantoinase from chromosomal DNA.

The process according to the invention starts here from chromosomal DNA of an organism which is capable of conversion of 5'-substituted hydantoins into D-amino acids. This is broken up into fragments by techniques known to the expert (the restriction digestion is carried out here e.g. in accordance with the instructions of the manufacturer of the restriction kit {Roche diagnostics}). The DNA fragments are then cloned into suitable plasmids analogously to known measures (Sambrook J, Fritsch E F, Maniatis T (1989). Molecular Cloning. Cold Spring Harbour Laboratory Press). The plasmids mentioned above can be regarded as suitable. The hybridization of the plasmid DNA with the DNA of a suitable enzyme is in turned achieved by hybridization techniques known to the expert (Sambrook J, Fritsch E F, Maniatis T (1989). Molecular Cloning. Cold Spring Harbour Laboratory Press), it being possible for the successful hybridization to take place e.g. by means of DNA amplification (PCR), marking (fluorescence, radioactivity) of the oligonucleotides or by means of expression libraries and activity detection. Starting from a hybridization signal, the adjacent regions are identified and analysed in respect of the presence of a D-hydantoinase or D-carbamoylase, for example, via an IPCR (Genetic applications of an inverse polymerase chain reaction, Ochman H, Gerber A S, Hartl D L, GENETICS (1988 November), 120(3), 621–3; The polymerase chain reaction, Arnheim, Norman, Genet. Eng. (N.Y.) (1990), 12 115–37) of the known hybridized gene via conventional DNA sequencing and sequence comparison or activity detection. This is also carried out by methods with which the expert is familiar, i.e. via DNA sequencing and analysis of the DNA sequence by appropriate programs, such as e.g. the GCG program (see also Molecular Cloning: A Laboratory Manual, Joseph Sambrook and David W. Russell, Cold Spring Harbor Laboratory Press, 2000).

In the context of the invention, optically concentrated (enantiomerically concentrated, enantiomer-concentrated) compounds is understood as meaning the presence of an optical antipode as a mixture with the other in >50 mol %. Such concentrated compounds may preferably be >55, 60, 65 or 75 mol % concentrated for the a particular enantiomer. More preferably >80, 85, 90, 95 or 99 mol % concentrated for a particular enantiomer.

Hydantoins means the compounds which are derived from 2,4-dioxo-imidazolidines and which are substituted in the 5-position by a radical which can be derived from the α-radical of an amino acid.

α-Radical of an amino acid is understood as meaning the radical on the α-C atom of an α-amino acid. This can be derived from a natural amino acid, as described in Beyer-Walter, Lehrbuch der organischen Chemie, Textbook of Organic Chemistry, S. Hirzel Verlag Stuttgart, 22nd edition, 1991, p.822 et seq. Furthermore, however, it is also understood as meaning corresponding α-radicals of non-natural α-amino acids, as described e.g. in DE19903268.8.

The organism *Arthrobacter crystallopoietes* DSM 20117 has been deposited at the Deutsche Sammlung für Mikroorganismen und Zellkulturen, German Collection of Microorganisms and Cell Cultures, under the corresponding number and is accessible to the public.

Where the enzyme according to the invention is mentioned, this means both the native homogeneously purified enzyme and the corresponding enzyme or polypeptide enzymatic activity, for instance, as prepared by a recombinant process. This also includes all further enzymes with the same peptide sequence or same activity in respect of the sequences which influence the reaction, but which have been modified, e.g. His-tag-modified enzymes or start codon-modified enzymes etc.

EXAMPLES

I. Obtaining Biomass of *Arthrobacter crystallopoietes* DSM 20117

As the starting material for whole cell activity tests, for the isolation of chromosomal DNA and for enzyme isolation of D-hydantoinase, a physiologically uniform cell mass of *Arthrobacter crystallopoietes* DSM 20117 should first be provided in a sufficient amount. According to the work of Brans (doctorate thesis, TU Braunschweig, 1991), a semi-synthetic medium with D,L-lactate as the source of carbon, yeast extract as a further constituent and hydantoin as an inductor for the culture in a 50 liter bioreactor was used for this.

TABLE 1

| Nutrient solution (ingredients per liter) | | |
|---|---|---|
| Sodium lactate medium pH 7.2 (V = 1 litre) (Brans, 1991) | Citric acid | 0.75 g |
| | Yeast extract | 1.0 g |
| | $FeSO_4 * 7 H_2O$ | 0.01 g |

TABLE 1-continued

| Nutrient solution (ingredients per liter) | |
|---|---|
| $MgSO_4 * 7 H_2O$ | 0.5 g |
| $CaSO_4 * 2 H_2O$ | 0.22 g |
| $MnSO_4 * H_2O$ | 0.055 g |
| $ZnSO_4 * 7 H_2O$ | 0.005 g |
| $(NH_4)_2SO_4$ | 6.0 g |
| D,L-Methionine | 0.05 g |
| Hydantoin | 1.0 g |
| 50% D,L-lactate | 40 ml |
| 1 M $KH_2PO_4$ | 23 ml |

A first preculture (V=20 ml) was incubated overnight at 30° C. and 110 rpm. The entire preculture was then used for inoculation of the second preculture (V=2 l). After incubation for two day, 1.5 l of the second preculture was used as the inoculum for the fermentation (V=20 l). Since the inductor hydantoin is consumed during the growth, this was metered in continuously with a delivery pump, so that the hydantoin concentration in the medium was a constant 0.2 g/l. After harvesting of the cells, 205 g BFM was divided into aliquots and stored at −20° C.

II. Purification of the D-hydantoinase from *Arthrobacter crystallopoietes* DSM 20117

The protocol for purification of the D-hydantoinase from *Arthrobacter crystallopoietes* DSM 20117 is orientated with some modifications on the protein purification of D-hydantoinase described by Marin (doctorate thesis, Uni Stuttgart, 1997). The purification steps were, if possible, carried out at 4° C. and the determination of the hydantoinase activity of the fractions was initially carried out in the quick test with photometric detection by the method of Ehrlich. Aliquots of the positive samples were then incubated with the standard substrate D,L-benzylhydantoin and the exact activity was determined by means of HPLC.

The biomass obtained from the culture (see I) of *Arthrobacter crystallopoletes* DSM 20117 was first subjected as a 30% cell suspension to breakdown by glass beads in a stirred ball mill. After recording the breakdown kinetics, protein concentrations of up to 16.5 g/l were to be achieved after a breakdown time of 20 minutes. The cell debris and insoluble constituents were then separated off by centrifugation and the clarified supernatant was employed for the following protamine sulfate precipitation. The viscosity of the solution could be reduced with this before a streamline DEAE column chromatography was carried out.

The proteins bound on the column were eluted by means of a sodium chloride gradient. An equal volume of 2 M $(NH_4)_2SO_4$ was added to the active, pooled streamline fractions in order to subsequently separate them further by means of hydrophobic interaction chromatography (HIC). The fractions with the highest hydantoinase activity were then combined and separated from other proteins via anion exchange chromatography on a MonoQ column.

The data on purification of the hydantoinase are summarized in table 2, the SDS-PAGE of the purified D-hydantoinase gave a molecular weight of 50 +/− 5 kDa for this enzyme {10% SDS-PAGE of the purified D-hydantoinase after concentration of the MonoQ fractions, molecular weight marker ProSieve and L-hydantoinase from A. aurescens DSM 3745 as an internal standard of 49.7 kDa (May, dissertation Uni Stuttgart, 1998)}.

TABLE 2

Purification data for the D-hydantoinase

| Purification | Vol. [ml] | Prot. [g/l] | Spec. act. [U/mg] | Purification factor | Yield [%] |
|---|---|---|---|---|---|
| Cell breakdown | 32 | 16 | 1.5 | — | 100 |
| Protamine sulfate precipitation | 29 | 17 | 1.4 | 0.9 | 89 |
| Combined streamline frac. | 61 | 3.8 | 1.9 | 1.3 | 57 |
| Supernatant ammonium sulfate precip. | 120 | 1.5 | 3.7 | 2.4 | 85 |
| Combined HIC fractions | 30 | 0.8 | 13.3 | 8.8 | 41 |
| Combined MonoQ fractions | 19 | 0.4 | 30.1 | 19.8 | 29 |

III. Tryptic Digestion of the D-hydantoinase

N-terminal sequencings give reliable sequence results only for the first 30 amino acids. The sequence given in the work by Marin, however, did not allow primers to be derived. The protein therefore had to be divided into several peptides by a protease digestion for further sequence information. For enzymatic fragmentation an endopeptidase which cleaves specifically after the amino acids lysine and arginine was used with trypsin. However, a reduced activity is to be expected if an acidic amino acid follows, and even an absence of hydrolysis if a proline radical follows. With an average occurrence of lysine and arginine in proteins of 5.7% and 5.4% respectively, an average peptide length of about 9 amino acids is to be expected on complete digestion. The peptide mixture was then separated by quantitative HPLC.

To digest the hydantoinase from *Arthrobacter crystallopoietes* DSM 20117 with trypsin, this was purified up to the MonoQ fractions as described and then concentrated with an Amicon filter (cut-off 30 kDA) and separated by means of SDS-PAGE. To ensure that the protein was also D-hydantoinase, a portion of the gel was transferred to a membrane via a western blot and cut out and the first eight amino acid N-terminally were determined. With the exception of position 2, all the amino acids determined coincided with the N-terminus determined by Marin (dissertation, University of Stuttgart, 1997), so that it could be assumed that the protein isolated here was the same enzyme which has already been described and characterized by Marin.

The hydantoinase band was then cut out directly from the polyacrylamide gel of the separated MonoQ fractions and subjected to trypsin digestion in situ in accordance with the manufacturer's instructions (Sigma, Steinheim). The peptides were extracted from the gel with acetonitrile and separated from one another by means of preparative HPLC. The fractions were dried out in a Speed-vac and then sequenced N-terminally via Edman degradation.

Overall, in addition to the N-terminus, nine peptides could be unambiguously sequenced. One of the peptide fragments had the consensus motif GXXDXHXH (SEQ ID NO: 14) of cyclic amidases, which participates in the binding of a zinc atom in the active centre (Abendroth et al., Acta Cryst. 2000, D56, 1166–1169). The peptide sequences which do not end with a lysine (K) or arginine (R) interrupted the sequencing prematurely because of technical problems or a lack of quality or quantity of the samples.

IV. Cloning of the hyu Gene Cluster

1. Isolation of Chromosomal DNA from *Arthrobacter crystallopoietes* DSM 20117

The moist biomass obtained by culture of *Arthrobacter crystallopoietes* DSM 20117 on lactate medium (see I) was also used for isolation of chromosomal DNA. After cell lysis and purification by means of caesium chloride density gradient centrifugation, highly pure, genomic DNA could be isolated. The quality was tested by recording an absorption spectrum in order to be able to rule out contamination with phenol in this way. The photometrically determined DNA concentration was 60 µg DNA/ml.

The cDNA was employed for a restriction digestion and used as the matrix for PCRs.

2. PCR with Degenerated Primers

In addition to the N-terminus of the D-hydantoinase, further sequence information could be obtained by sequencing of the peptides originating from the tryptic digestion (see III). The peptides were matched with the ClustalX program to the known protein sequence of Agrobacterium sp. IP I-671 (Thompson et al. 1997, The ClustalX windows interface: flexible strategies for multiple sequence alignment aided by quality analysis tools. Nucleic Acids Research. 24, 4876–4882).

To derive degenerated primers from the known peptide sequences, sequence sections of two peptides which have a low degree of degeneration in the amino acid composition should be chosen. The peptides 61.61 and 73.31 were chosen for this. The primer 61.61a pairs to the plus strand and the primer 73.31b to the minus strand of the DNA.

TABLE 3

Construction of the degenerated primers

| Peptide | DNA sequence derived | Primer Seq. name |
|---|---|---|
| SLVMYETGVAEGK (61.61 SEQ ID NO: 12) | 5'-GT(AGCT) ATG TA(CT) GA(AG) AC(AGC) GG-3' | 61.61a 10 |
| QNMDYTLFEGK (73.31 SEQ ID NO: 13) | 5'-GT(AG) TA(AG) TCC AT (AG) TT(CT) TC-3' | 73.31b 11 |

To reduce the degree of degeneration of the primer 61.61a further, the frequency distribution of the codon from Arthrobacter sp. was taken into consideration on the basis of the CUTG databank (Nakamura et al., Nucl. Acids Res. 1999, 27, 292). The base triplet "GTA" at position 3 of this oligonucleotide could be ignored in the primer construction as a result because of the low probability of this codon of 10.4% for the amino acid valine.

To estimate the length of the PCR amplicon, an alignment of the two primers to the D-hydantoinase from Agrobacterium sp. IP I-671 was carried out. In the alignment, the distance between the two oligos is 69 amino acids, so that a PCR with the degenerated primers 61.61a and 73.31b should lead to a PCR product of approx. 207 bp in length.

Figure 3:
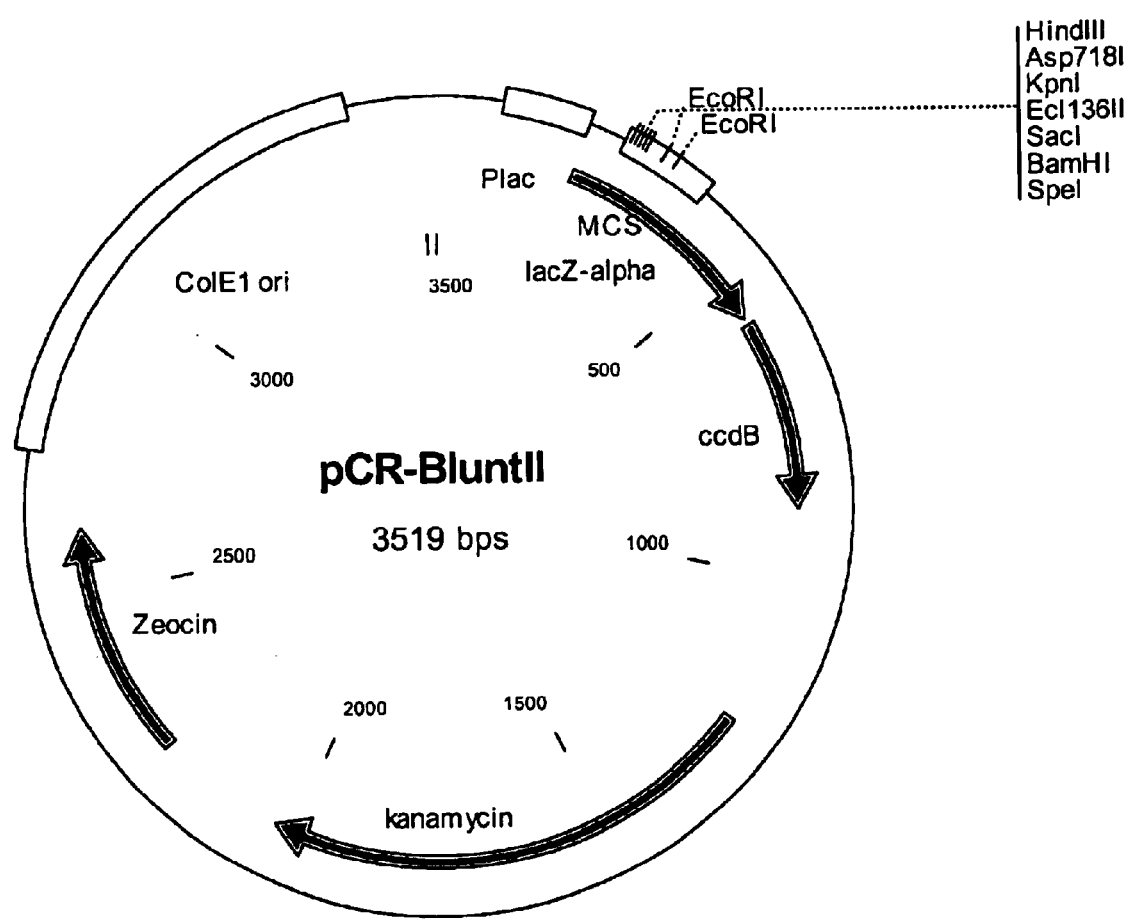
FIG. 3 depicts plasmid pCR-BluntII.
Figure 4:
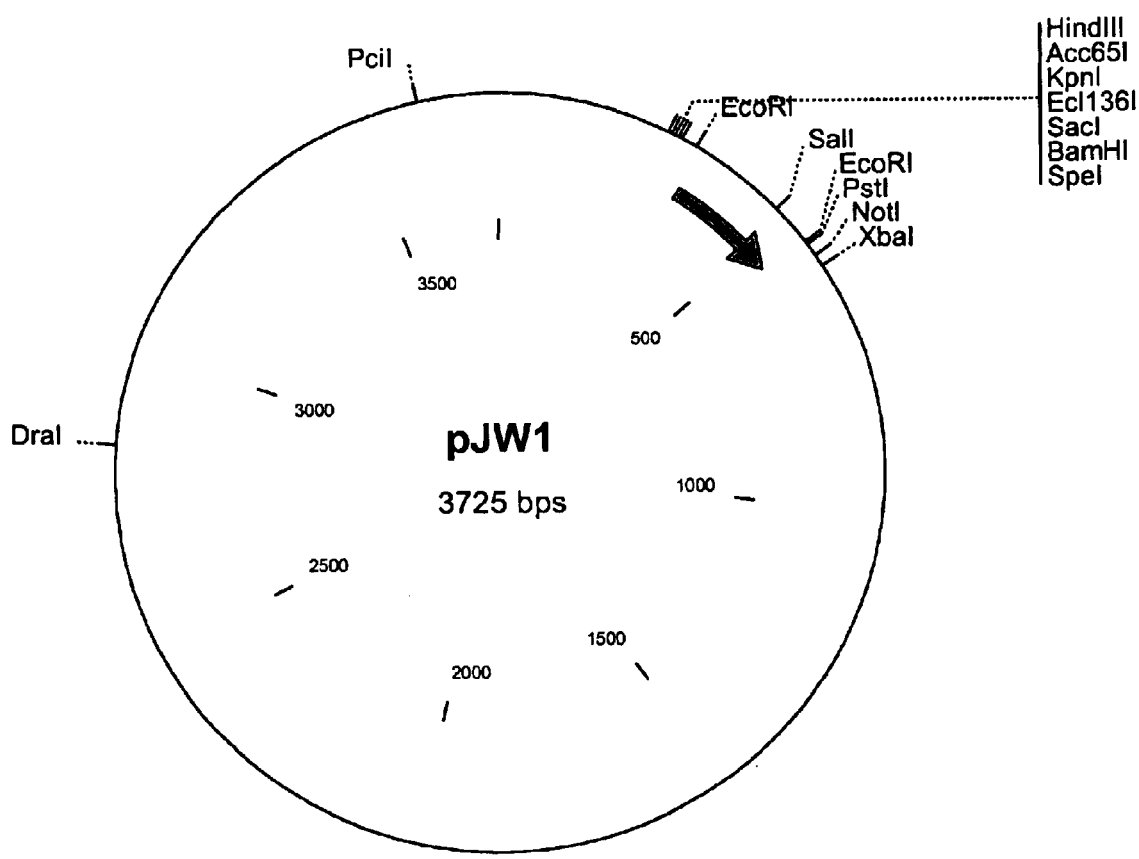
FIG. 4 depicts plasmid pJW1.

The PCR was set up in the temperature profile according to the standard batch at an annealing temperature of 42° C. and optimized to a concentration of 2 mM in respect of the magnesium content. The PCR batch was then separated in a 3% agarose gel and the size of the bands was determined with the Imagemaster image analysis software (molecular weight marker D-15 from Novex). The band which had a calculated size of 218 bp was eluted from the gel and ligated into the pCR TOPO BluntII vector (FIG. 3). The plasmid obtained was called pJW1 (FIG. 4). Subsequent sequencing of the vector showed homologies to already known dihydropyrimidinases, so that the first DNA section was thus present in cloned form on the structural gene of D-hydantoinase.

3. Sequencing of the hyu Gene Cluster via an Inverse PCR

To obtain further sequence information from the flanking DNA regions, the technique of the inverse PCR (PCR) was employed.

The restriction enzymes BamHI, EcoRI, SacI, PstI, BglII, HindIII, SalI, MunI, and MluI were used for digestion of genomic DNA from *Arthrobacter crystallopoietes* DSM 20117. The digested products were separated over a 1% agarose gel and fixed on a nylon membrane by means of a southern blot.

To prepare a suitable probe, the MunI linearized plasmid pJW1 (FIG. 4) was radioactively labelled with $^{32}P$-$\alpha$-ATP via Nick Translation (Nick Translation Kit from Roche Diagnostics) and employed for hybridization with the blot (molecular weight marker MWM VII).

On the basis of the size of the hybridization signals obtained from the southern blot, the genomic PstI digestion product (approx. 2000 bp) was used as the matrix in the following IPCR. For this, the digestion product was separated on an agarose gel, eluted from the gel in the range between 1500 and 2800 bp (molecular weight marker MWM VII), and then religated and linearized with MunI. From the known sequence of the hydantoinase gene, the primers IPCR1+ (seq. 3) and IPCR1-(seq. 4) for the IPCR could be derived. The annealing temperature of 60° C. was derived from the melting temperatures of the oligos.

A single band could be generated as the amplicon, which was then eluted and cloned in the TOPO system (FIG. 3). The plasmid formed was called pJW2 (FIG. 1). The hyu gene cluster reconstructed after the sequencings of pJW2 contains the open reading frame of D-hydantoinase hyuH and a portion of the open reading frame of D-carbamoylase hyuC$_D$.

In the next step, the complete reading frame of the D-carbamoylase should be cloned, likewise via the technique of the IPCR. For this, restriction enzymes which met the requirements of the IPCR and should cleave as far as possible at the 5' end of the D-carbamoylase gene could be found from the known sequence section of D-carbamoylase. Finally, a genomic digestion was carried out with the restriction enzymes SacI, NaeI, SfuI, NarI and SphI and, after separation in agarose gel, blotting on a nylon membrane was carried out.

The small fragment of an NarI/BamHI double digestion of pJW1 was suitable as a probe (FIG. 4). Separation in a gel, elution and subsequent radioactive labelling by means of Nick Translation (Nick Translation Kit from Roche Diagnostics) were carried out and the product was employed for the hybridization.

On the basis of the hybridization signals, the religated NarI digestion product (1.4 kb) was chosen as the DNA template for the second IPCR. The oligos IPCR5+ (seq. 5) and IPCR5-(seq. 6) were employed as primers at an annealing temperature of 57° C.

Figure 2:
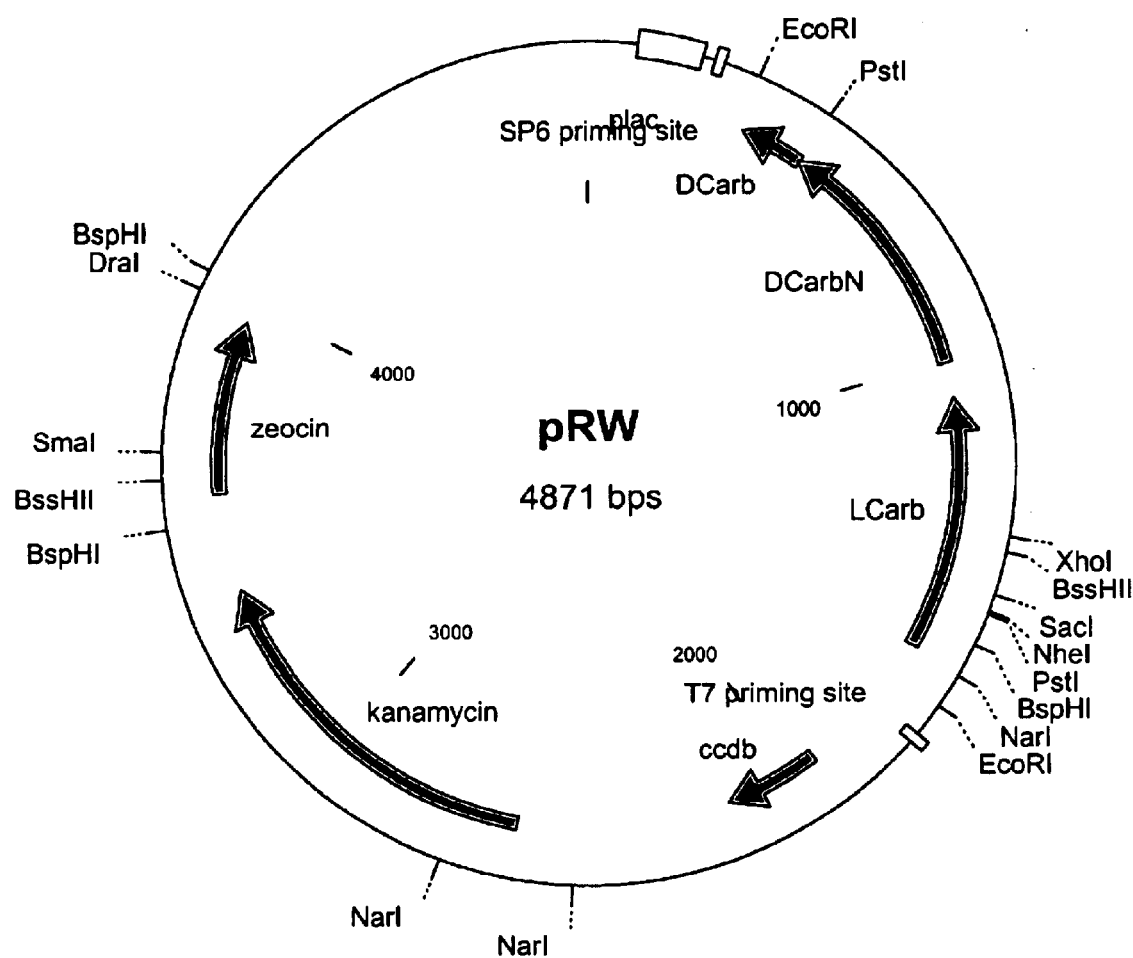
FIG. 2 depicts plasmid pRW.

The band was cloned into the TOPO vector (FIG. 3) and the TOPO plasmid formed was called pRW (FIG. 2). After sequencing of the insert, the hyu gene cluster could be reconstructed to the extent that the reading frame of the D-carbamoylase was present in full.

V. Expression of the D-carbamoylase

After the sequencing of the hyu gene cluster had been concluded, an investigation of the DNA sequence for potential reading frames took place. In addition to the atg start codon, an unusual ttg start codon is also possible here for the translation start of the D-carbamoylase, this codon leading to an N-terminus lengthened by five amino acids. Since in spite of the indications no clear proof of the presence of a rare ttg start codon could be produced, both the ttg- and the atg-D-carbamoylase were cloned and tested in respect of their expression and activity in *Escherichia coli*.

For this, the D-carbamoylases were amplified from the genomic DNA of *Arthrobacter crystallopoietes* DSM 20117 by means of the PCR. Different primer pairs were employed here, so that it was possible to clone three different D-carbamoylases. One D-carbamoylase with the atg start codon without the His-tag and two D-carbamoylases with the ttg start codon. One of these with, the other without the His-tag. In the primer construction, the ttg base triplet from the Arthrobacter sequence was replaced in *Escherichia coli* by an atg codon (table 4).

TABLE 4

Properties of the various clones of the D-carbamoylase

Figure 5:
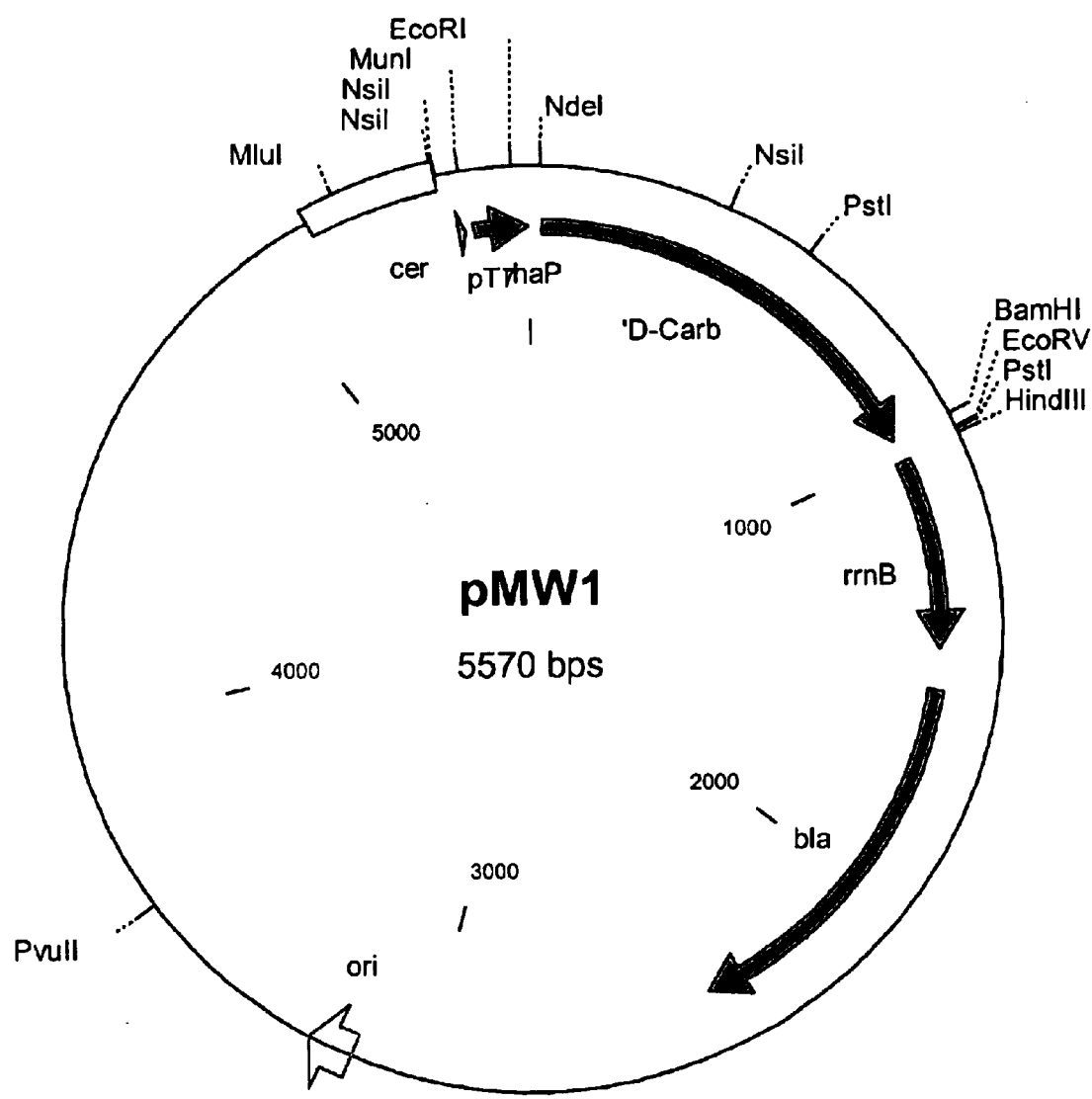
FIG. 5 depicts plasmid pMW1.
Figure 6:
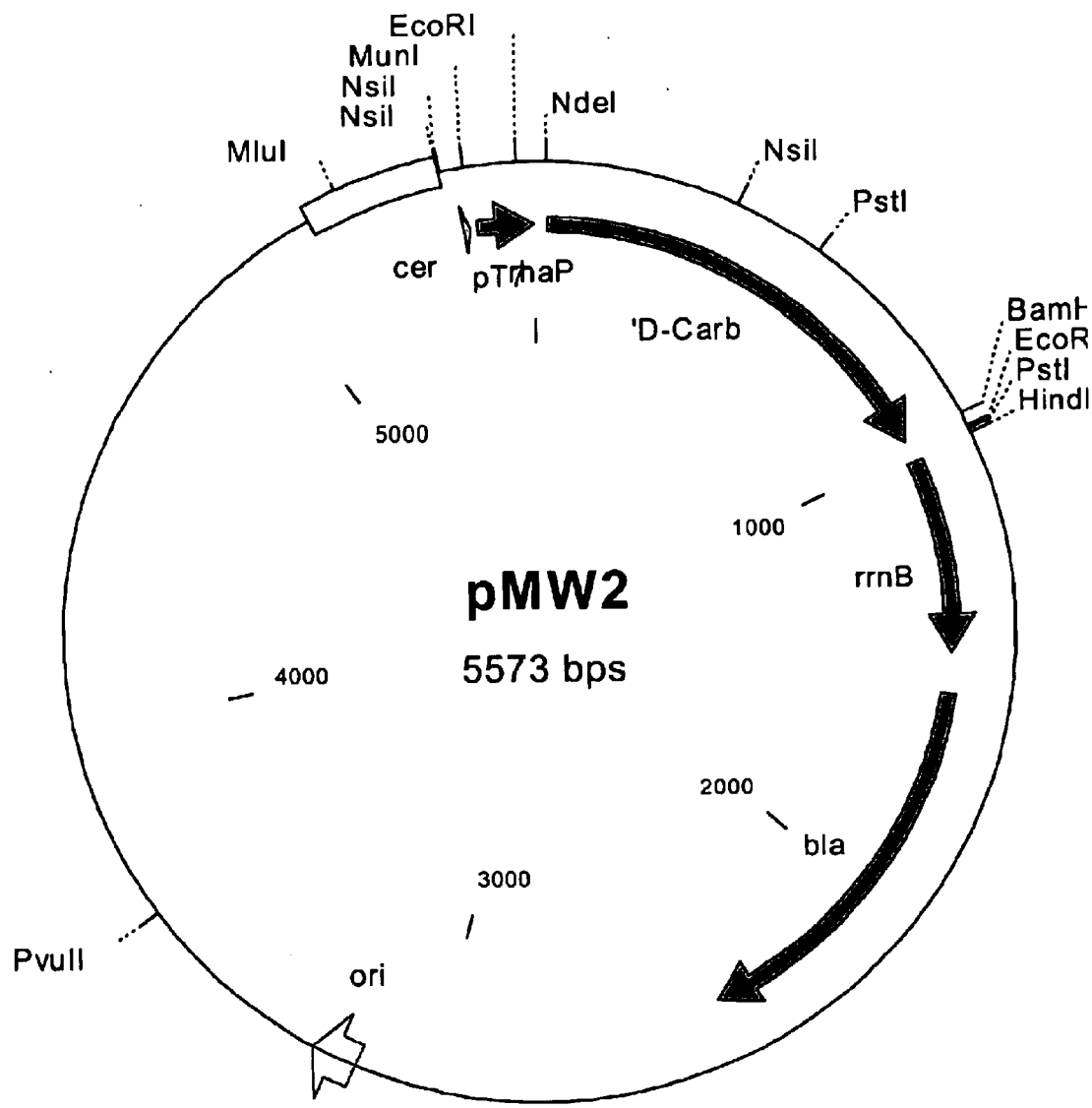
FIG. 6 depicts plasmid pMW2.

| Plasmid name | pMW1 (FIG. 5) | pMW2 (FIG. 6) | pMW3 (FIG. 5) |
| --- | --- | --- | --- |
| Start codon in Arthrobacter | ttg | ttg | atg |
| Primer pair | K_DCn2/c2 | K_DCn2/c3 | K_DCn1/c2 |
| N-terminal restriction site | NdeI | NdeI | NdeI |
| C-terminal restriction site | BamHI | BamHI | BamHI |
| His$_6$-tag | yes | no | no |

Figure 7:
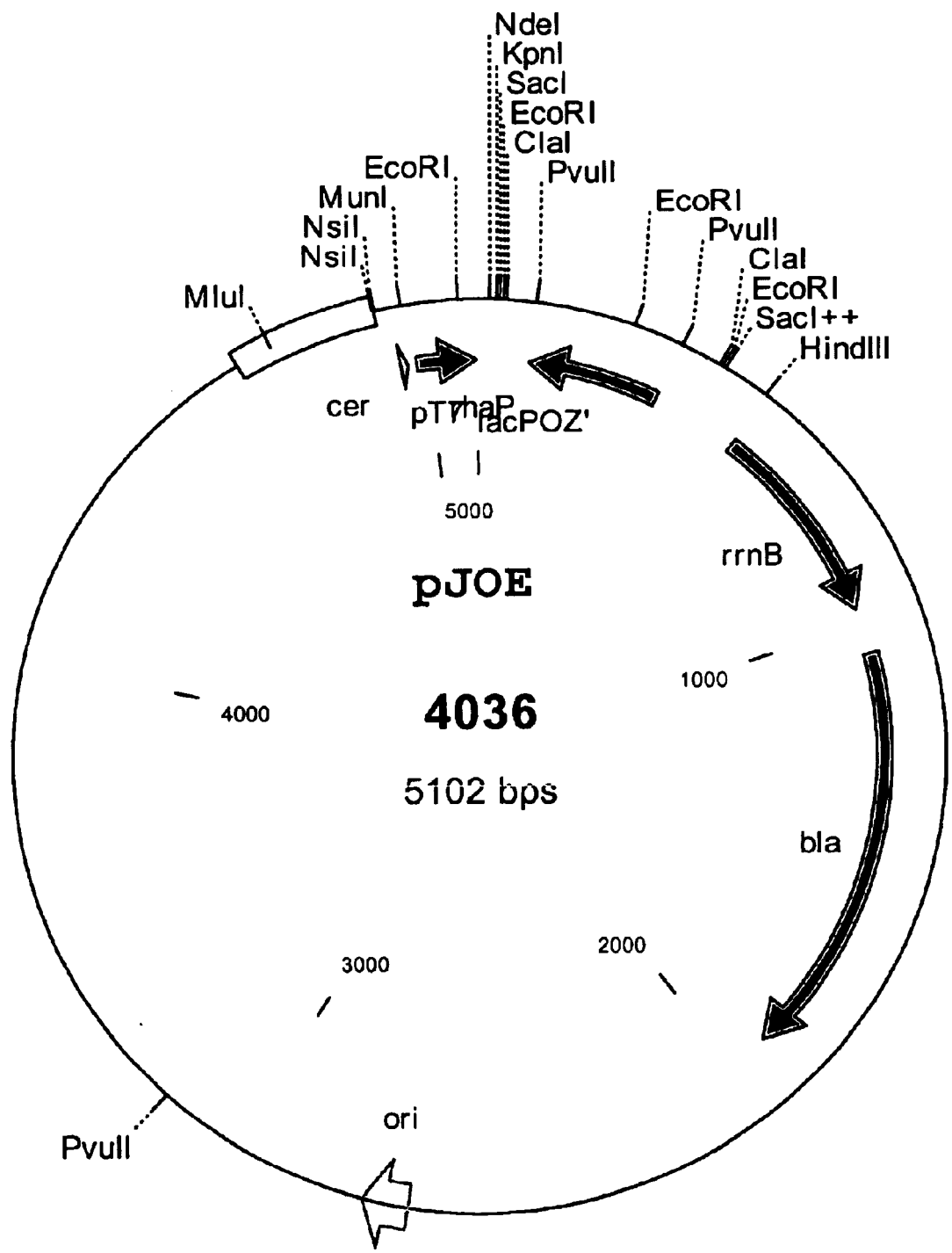
FIG. 7 depicts plasmid pJOE4036, a rhamnose expression vector.

The amplicons were cloned into the vector pCR TOPO BluntII (FIG. 3) and the plasmid formed was subjected to a double digestion with the restriction enzymes NdeI and BamHI. The rhamnose expression vector pJOE4036 (FIG. 7) was used for subcloning the fragment formed 947 bp in size. The plasmids were transformed in *Escherichia coli* JM109 and the cells were induced with 0.2 g/l rhamnose at the start of the exponential phase.

No increasing protein band at the level of D-carbamoylase (34 kDA) is to be detected with the atg start codon alternative, while a clear increase is to be recorded in the D-carbamoylase with the ttg start codon. After induction for 20 hours, the intensity of the recombinant protein band decreases again, however, which is probably to be attributed to a proteolytic digestion of the protein.

After cell breakdown of the two clones with a homogenizer, D-carbamoylase activity was to be found only with the clone with the ttg start codon, while the activity for pMW3, which differs from pMW1 only with respect to the start codon, remained below the detection limit.

The D-carbamoylase is present predominantly in the supernatant. The molecular weight of the expressed protein could be specified as 34.6 kDa with the aid of the Image Master program (Amersham Life Sciences, Freiburg). This molecular weight is in good agreement with the value calculated for the D-carbamoylase with the His-tag (35.4 kDa). It could also be determined with the aid of this program that the content of D-carbamoylase in the supernatant makes up 30% of the total protein. After recording an expression profile, it was to be found that the expression maximum is reached after an induction time of approx. six hours. The specific activity also shows its maximum at this point in time (2 U/mg for DL-C-Phe).

VI. Purification of the D-carbamoylase

In order to be able to characterize the D-carbamoylase, it was purified. In the purification process, biomass of the corresponding recombinant Escherichia coli strain was first cultured and the cell suspension was broken down with a homogenizer (see II). The D-carbamoylase contained in the supernatant was then purified via metal affinity chromatography (Talon® columns from Stratagene). By rebuffering in 0.1 KPB, pH 8.0, by means of gel filtration (by means of PD-10 columns from Pharmacia) the imidazole contained in the elution buffer of the Talon column was removed. The individual purification steps were documented by means of SDS-PAGE.

VII. Characterization of the D-carbamoylase

The homogeneously purified D-carbamoylase with the His-tag and ttg start codon (pMW1 —FIG. 5) was used for characterization of the enzyme obtained in this way. The enzyme was present in 0.1 M KPB pH 8.0.

1. Determination of the Optimum pH

To determine the optimum pH of the purified D-carbamoylase, conversions were carried out at various pH values in a range from 6.5 to 9.0 with DL-C-phenylalanine as the substrate at 30° C. In order to be able to rule out concentration effects, the buffer concentration of all the buffers used (Tris, potassium phosphate and Tris-glycine) was adjusted to a value of 100 mM. The activity maximum of the D-carbamoylase was at pH 8.

2. Heat Stability

In order to investigate the heat stability of the D-carbamoylase at 4° C., the enzyme was stored in 0.1 M KPB at pH 8.0 over a period of 4 days in the refrigerator and a measurement value was taken every 24 hours. At this temperature the half-life of the enzyme is approximately 100 hours.

Figure 8:
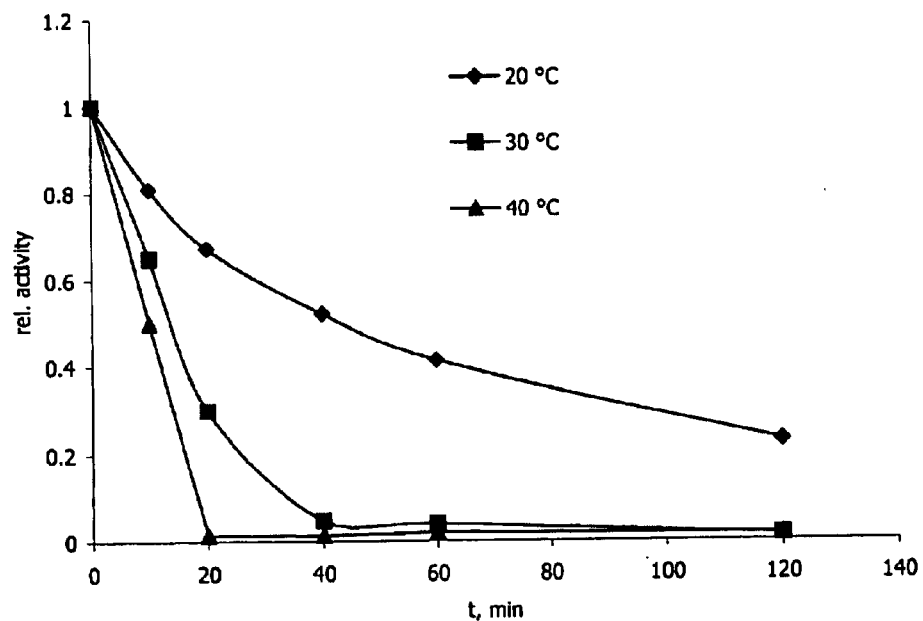
FIG. 8 shows the heat stability of D-carbamoylase at 20, 30 and 40° C.

In order to determine the heat stability at 20, 30 and 40° C., the enzyme was incubated for 40 min at the particular reaction temperature and the activity was determined every 5 min. The results are shown in FIG. 8.

3. Determination of the Optimum Temperature

In order to determine the optimum temperature, the conversion of D,L-carbamoyl-phenylalanine was carried out under the conditions of the standard assay at various temperatures. The optimum for the reaction temperature is about 30° C.

4. Determination of Kinetic Parameters

Figure 9:
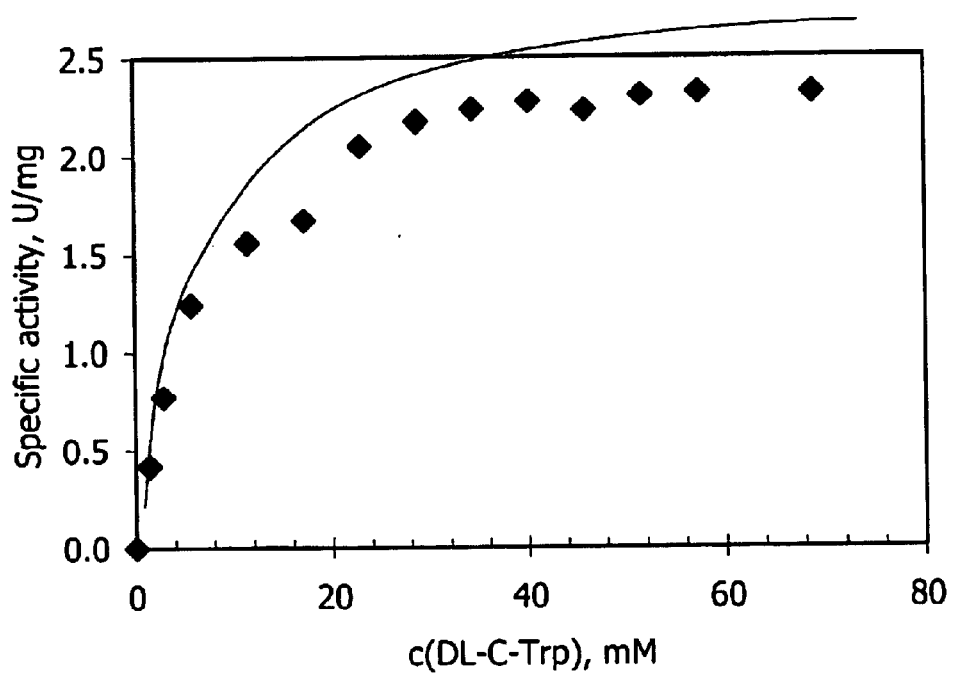
FIG. 9 shows kinetic parameters for D-carbamoyl-tryptophan. The rate of reaction ("v") is shown as a function of the substrate concentration.

For determination of $V_{max}$ and $K_m$, the rate of reaction v was plotted as a function of the substrate concentration. The plot for D-carbamoyl-tryptophan is shown in FIG. 9. The calculation of the kinetic parameters was carried out via the Enzymfit program (developed at the Institute of Bioprocess Technology, University of Stuttgart). For D-carbamoyl-tryptophan, the $K_m$ value is 7.5 mM and $v_{max}$ is 2.4 U/mg. The reaction can be described here by Michaelis-Menten kinetics (see equation 1).

$$r = \frac{r_{max} \cdot [S]}{K_m + [S]}$$

Equation 1: Michaelis-Menten kinetics
$r_{max}$ maximum rate of reaction
S substrate concentration
$K_m$ Michaelis-Menten constant

5. Determination of the Molecular Weight

The determination of the molecular weight under denaturing conditions in SDS gel with the Imagemaster program (Amersham Life Sciences, Freiburg) gave a value of 34.6 kDa. This value is in good agreement with the value calculated on the basis of the amino acid sequence of the D-carbamoylase with the His-tag (35.46 kDA). To ascertain whether the enzyme is present in the mono- or oligomeric state in the native state, a native gel electrophoresis was carried out with the homogeneously purified His-tag enzyme at an acrylamide concentration of 7.5 wt. %. At this concentration the linear range of the separation is between 16 and 91 kDa. After calibration of the gel with the protein marker ProSieve, the molecular size of the D-carbamoylase was determined with Imagemaster program as 75 kDa. The enzyme accordingly appears to be present as a dimer in the native state.

6. Cofactor Dependence

In an incubation of the purified D-carbamoylase at 25° C. and in the presence of 10 mM EDTA, no inactivation of the enzyme was to be found. Nevertheless, a compete inhibition of the enzyme was to be observed within less than two hours when it was incubated with 10 mM 8-hydroxyquinolinesulfonic acid (8-HQSA). In order to be able to differentiate the inactivation by the complexing agent from the thermal inactivation, an aliquot of the enzyme solution was co-incubated without 8-HQSA and the activity was monitored with respect to time. It was concluded that to reactivate the enzyme, the 8-HQSA had to be removed from the enzyme by gel filtration, and incubation had to be carried out in the presence of 2 mM metal ions. However, neither $Cu^{2+}$, $Co^{2+}$, $Mn^{2+}$, $Mg^{2+}$, $Fe^{2+}$ nor $Zn^{2+}$ led to a reactivation of the enzyme.

Sulfhydryl reagents (iodine acetate, 2-nitrobenzoate and para-chloro-mercury benzoate) added to the enzyme in concentrations of 1 mM led to a complete inactivation of the D-carbamoylase.

7. Substrate Specificity

To determine the substrate spectrum, the enzyme was incubated at a reaction temperature of 30° C. with the particular substrate in the presence of 0.1 M potassium phosphate buffer pH 8.0. To ensure the same concentration of the D-isomer, if the substrate was present as an isomer mixture a concentration of 20 mM was established; if the substrate was present as a pure isomer a concentration of 10 mM was established. D,L-Carbamoyl-phenylalanine was used here as the reference substrate and was set at 100% (corresponds to 2 U/mg) in the calculation of the relative activities. The carbamoyl substrates shown with structural formulae in table 5 were converted with the particular activities. The D-carbamoylase from Arthrobacter crystallopoietes DSM 20117 is capable of converting carbamoyl compounds with aliphatic and with aromatic radicals, the latter being converted faster. A characteristic feature of the D-carbamoylase found is, for example, the clear preference for the substrate D-carbamoyl-alanine, which is converted at least five times better than all other substrates. As the only achiral substrate among the compounds tested, carbamoyl-glycine is converted with similar reaction rates to the carbamoyl-amino acids with aliphatic radicals.

TABLE 5

Structural formulae, abbreviations and relative conversions of the D-carbamoylase substrates

| Substrate | Formula of the amino acid radical | Abbreviation | Rel. act. [%] |
|---|---|---|---|
| D,L-Carbamoyl-phenylalanine | (benzyl) | D,L-C-Phe | 100 |
| D-Carbamoyl-phenylalanine | see D,L-C-Phe | D-C-Phe | 115 |
| L-Carbamoyl-phenylalanine | see D,L-C-Phe | L-C-Phe | 0 |
| D,L-Carbamoyl-para-chloro-phenylalanine | (4-chlorobenzyl) | D,L-p-Cl-C-Phe | 19 |
| D-Carbamoyl-tryptophan | (indolylmethyl) | D-C-Phe | 80 |
| D,L-Carbamoyl-tyrosine | (4-hydroxybenzyl) | D,L-C-Tyr | 63 |
| D,L-Carbamoyl-pyridylalanine | (pyridylmethyl) | D-C-Pal | 43 |
| D-Carbamoyl-alanine | H$_3$C— | D,L-C-Ala | 510 |
| Carbamoyl-glycine | H— | C-Gly | 27 |
| D,L-Carbamoyl-valine | (CH$_3$)$_2$CH— | D,L-C-Val | 31 |
| D,L-Carbamoyl-serine | HO— | D,L-C-Ser | 35 |
| D,L-Carbamoyl-tert-leucine | (CH$_3$)$_3$C— | D,L-C-tLeu | 18 |
| D,L-Carbamoyl-methionine | CH$_3$S-CH$_2$-CH$_2$— | D,L-C-Met | 13 |
| β-Ureido-propionate | —COOH | β-UP | 0 |
| β-Ureido-succinate | HOOC— —COOH | D,L-C-Asp | 0 |

Amino acids with non-natural radicals, such as, for example, D,L-para-chloro-phenylalanine, D,L-carbamoyl-tert-leucine or D,L-carbamoyl-pyridylalanine, can also be detected as the reaction product after conversion of the corresponding substrates.

On comparison of the conversion of D,L-, D- and L-carbamoyl-phenylalanine, it can be seen that the enzyme is enantiospecific for this substrate and that the racemic mixture is converted reproducibly more slowly than the pure D-isomer The L-isomer thus seems to have a slight inhibitory effect on the enzyme catalysis at concentrations of 10 mM, since the same concentration of the D-isomer was present in the batches with D- and D,L-carbamoyl-phenylalanine.

Other pure L-carbamoyl-amino acids, such as L-carbamoyl-valine or L-carbamoyl-tryptophan, were also not converted.

β-Ureidopropionate and β-ureidosuccinate (D,L-carbamoyl-aspartate) were furthermore tested as a possible physiological substrate. Both compounds are not converted under the assay conditions chosen.

Modifications and Other Embodiments

Various modifications and variations of the described nucleic acid and polypeptide products and compositions, as well as methods of making or using such and the concept of the invention will be apparent to those skilled in the art without departing from the scope and spirit of the invention. Although the invention has been described in connection with specific preferred embodiments, it should be understood that the invention as claimed is not intended to be limited to such specific embodiments. Various modifications of the described modes for carrying out the invention which are obvious to those skilled in the molcular biological, medical, biological, chemical or pharmacological arts or related fields are intended to be within the scope of the following claims.

Incorporation by Reference

Each document, patent application or patent publication cited by or referred to in this disclosure is incorporated by reference in its entirety. Any patent document to which this application claims priority is also incorporated by reference in its entirety. Specifically, German priority document 101 14 999.9, filed Mar. 26, 2001 is hereby incorporated by reference.

What is claimed is:

1. An isolated polypeptide having D-carbamoylase activity encoded by an isolated or purified nucleic acid selected from the group consisting of:

a nucleic acid comprising SEQ ID NO: 1 or a fragment thereof, a nucleic acid that has at least 95% similarity to SEQ ID NO: 1 or a fragment thereof, and a nucleic acid that hybridizes under stringent conditions to the full complement of SEQ ID NO: 1, wherein stringent conditions comprise washing in 0.5×SSC at a temperature 68° C.

2. The polypeptide of claim 1 comprising SEQ ID NO: 2 or a fragment thereof having D-carbamoylase activity.

3. The polypeptide of claim 1 in multimeric form.

4. The polypeptide of claim 1 wherein the half-life of the D-carbamoylase activity at 4° C. is at least about 100 hours.

5. The polypeptide of claim 1, wherein the half-life of the D-carbamoylase activity at 4° C. is less than 100 hours.

6. The polypeptide of claim 1, wherein the activity maximum of the D-carbamoylase activity is less than or equal to pH 8.0.

7. The polypeptide of claim 1, wherein the activity maximum of the D-carbamoylase activity is at least pH 8.0.

8. The polypeptide of claim 1, wherein the optimum temperature for activity of the D-carbamoylase is less or equal to 30° C.

9. The polypeptide of claim 1, wherein the optimum temperature for activity of the D-carbamoylase is at least 30° C.

10. The polypeptide of claim 1, wherein the optimum temperature for activity of the D-carbamoylase is about 30° C.

11. A method for preparing an enantiomerically concentrated D-amino acid comprising:

converting a racemic N-carbamoyl amino acid into a D-amino acid using a polypeptide having D-carbamoylase activity encoded by an isolated or purified nucleic acid selected from the around consisting of: a nucleic acid comprising SEQ ID NO: 1 or a fragment thereof; a nucleic acid that has at least 95% similarity to SEQ ID NO: 1 or a fragment thereof, and a nucleic acid that hybridizes under stringent conditions to the full complement of SEQ ID NO: 1, wherein stringent conditions comprise washing in 0.5×SSC at a temperature of 68° C., and recovering or isolating said D-amino acid.

12. The method of claim 11, wherein said D-amino acid a hydrophobic amino acid.

13. The method of claim 11, wherein said D-amino acid is a positively charged amino acid.

14. The method of claim 11, wherein said D-amino acid is a negatively charged amino acid.

15. The method of claim 11, wherein said D-amino acid is an aromatic amino acid.

16. The method of claim 11, wherein said D-amino acid is an aliphatic amino acid.

17. The method according to claim 11, further comprising using a hydantoin racemase, a D-hydantoinase or a carbamoylamino acid racemase, or a combination thereof.

18. The method of claim 11, further comprising:

synthesizing a peptide, from said D-amino acid.

19. The method of claim 11, further comprising producing a nutritional product, cosmetic, medical or pharmaceutical product, drug, surfactant or agricultural chemical comprising:

incorporating said D-amino acid into said nutritional product, cosmetic, medical or pharmaceutical product, drug, surfactant or agricultural chemical.

20. The method of claim 11, further comprising esterifying or acetylating said D-ammo acid, or convening said D-amino acid into the corresponding alcohol.

21. The method of claim 11, wherein said polypeptide having D-carbamoylase activity is encoded by an isolated or purified nucleic acid that has at least similarity to SEQ ID NO: 1 or by a fragment thereof.

22. The method of claim 11, wherein said polypeptide having D-carbamoylase activity is encoded by an isolated or purified nucleic acid that hybridizes under stringent conditions to the full complement of SEQ ID NO: 1, wherein stringent conditions comprise washing in 0.5>SSC at a temperature of 68° C.

23. The method of claim 11, wherein said polypeptide having D-carbamoylase activity is encoded by a nucleic acid comprising SEQ ID NO: 1 or by a fragment thereof.

24. The method of claim 11, wherein said polypeptide having D-carbamoylase activity comprises SEQ ID NO: 2 or a fragment thereof having D-carbamyolase activity.

25. The isolated polypeptide of claim 1 which is encoded by an isolated or purified nucleic acid that has at least 95% similarity to SEQ ID NO: 1 or by a fragment thereof.

26. The isolated polypeptide of claim 1 which is encoded by an isolated or purified nucleic acid that hybridizes under stringent conditions to the full complement of SEQ ID NO: 1, wherein stringent conditions comprise washing in 0.5× SSC at a temperature of 68° C.

27. The isolated polypeptide of claim 1 which is encoded by a nucleic acid comprising SEQ ID NO: 1 or by a fragment thereof.

28. The isolated polypeptide of claim 1 which comprises SEQ ID NO: 2.

* * * * *

SEQUENCE LISTING

<160> NUMBER OF SEQ ID NOS: 14

<210> SEQ ID NO 1
<211> LENGTH: 948
<212> TYPE: DNA
<213> ORGANISM: ARTIFICIAL SEQUENCE
<220> FEATURE:
<223> OTHER INFORMATION: SYNTHETIC DNA
<220> FEATURE:
<221> NAME/KEY: CDS
<222> LOCATION: (1)..(948)
<223> OTHER INFORMATION:

<400> SEQUENCE: 1

```
atg gcg aaa aac ttg atg ctc gcg gtc gct caa gtc ggc ggt atc gat        48
Met Ala Lys Asn Leu Met Leu Ala Val Ala Gln Val Gly Gly Ile Asp
1               5                   10                  15 agt tcg gaa tca aga ccc gaa gtc gtc gcc cgc ttg att gcc ctg ctg        96
Ser Ser Glu Ser Arg Pro Glu Val Val Ala Arg Leu Ile Ala Leu Leu
            20                  25                  30 gaa gaa gca gct tcc cag ggc gcg gaa ctg gtg gtc ttt ccc gaa ctc       144
Glu Glu Ala Ala Ser Gln Gly Ala Glu Leu Val Val Phe Pro Glu Leu
        35                  40                  45 acg ctg acc acg ttc ttc ccg cgt acc tgg ttc gaa gaa ggc gac ttc       192
Thr Leu Thr Thr Phe Phe Pro Arg Thr Trp Phe Glu Glu Gly Asp Phe
    50                  55                  60 gag gaa tac ttc gat aaa tcc atg ccc aat gac gac gtc gcg ccc ctt       240
Glu Glu Tyr Phe Asp Lys Ser Met Pro Asn Asp Asp Val Ala Pro Leu
65                  70                  75                  80 ttc gaa cgc gcc aaa gac ctt ggc gtg ggc ttc tac ctc gga tac gcg       288
Phe Glu Arg Ala Lys Asp Leu Gly Val Gly Phe Tyr Leu Gly Tyr Ala
                85                  90                  95 gaa ctg acc agt gat gag aag cgg tac aac aca tca att ctg gtg aac       336
Glu Leu Thr Ser Asp Glu Lys Arg Tyr Asn Thr Ser Ile Leu Val Asn
            100                 105                 110 aag cac ggc gac atc gtc ggc aag tac cgc aag atg cat ctg ccg ggc       384
Lys His Gly Asp Ile Val Gly Lys Tyr Arg Lys Met His Leu Pro Gly
        115                 120                 125 cac gcc gat aac cgg gaa gga cta ccc aac cag cac ctt gaa aag aaa       432
His Ala Asp Asn Arg Glu Gly Leu Pro Asn Gln His Leu Glu Lys Lys
    130                 135                 140 tac ttc cgc gaa gga gat ctc gga ttc ggt gtc ttc gac ttc cac ggc       480
Tyr Phe Arg Glu Gly Asp Leu Gly Phe Gly Val Phe Asp Phe His Gly
145                 150                 155                 160 gtg cag gtc gga atg tgt ctc tgc aac gac cgg cga tgg ccg gag gtc       528
Val Gln Val Gly Met Cys Leu Cys Asn Asp Arg Arg Trp Pro Glu Val
                165                 170                 175 tac cgc tct ttg gcc ctg cag gga gca gag ctc gtc gtc ctg ggc tac       576
Tyr Arg Ser Leu Ala Leu Gln Gly Ala Glu Leu Val Val Leu Gly Tyr
            180                 185                 190 aac acc ccc gat ttc gtt ccc ggc tgg cag gaa gag cct cac gcg aag       624
Asn Thr Pro Asp Phe Val Pro Gly Trp Gln Glu Glu Pro His Ala Lys
        195                 200                 205 atg ttc acg cac ctt ctt tca ctt cag gca ggg gca tac cag aac tcg       672
Met Phe Thr His Leu Leu Ser Leu Gln Ala Gly Ala Tyr Gln Asn Ser
    210                 215                 220 gta ttt gtg gcg gct gcc ggc aag tcg ggc ttc gaa gac ggg cac cac       720
Val Phe Val Ala Ala Ala Gly Lys Ser Gly Phe Glu Asp Gly His His
225                 230                 235                 240 atg atc ggc gga tca gcg gtc gcc gcg ccc agc ggc gaa atc ctg gca       768
```

```
Met Ile Gly Gly Ser Ala Val Ala Ala Pro Ser Gly Glu Ile Leu Ala
                245                 250                 255 aaa gca gcc ggc gag ggc gat gaa gtc gtc gtt gtg aaa gca gac atc      816
Lys Ala Ala Gly Glu Gly Asp Glu Val Val Val Val Lys Ala Asp Ile
                260                 265                 270 gac atg ggc aag ccc tat aag gaa agc gtc ttc gac ttc gcc gcc cat      864
Asp Met Gly Lys Pro Tyr Lys Glu Ser Val Phe Asp Phe Ala Ala His
                275                 280                 285 cgg cgc ccc gac gca tac ggc atc atc gcc gaa agg aaa ggg cgg ggc      912
Arg Arg Pro Asp Ala Tyr Gly Ile Ile Ala Glu Arg Lys Gly Arg Gly
                290                 295                 300 gcc cca ctg ccc gtc ccg ttc aac gtg aat gac taa                      948
Ala Pro Leu Pro Val Pro Phe Asn Val Asn Asp
305                 310                 315

<210> SEQ ID NO 2
<211> LENGTH: 315
<212> TYPE: PRT
<213> ORGANISM: ARTIFICIAL SEQUENCE
<220> FEATURE:
<223> OTHER INFORMATION: SYNTHETIC DNA

<400> SEQUENCE: 2

Met Ala Lys Asn Leu Met Leu Ala Val Ala Gln Val Gly Gly Ile Asp
1               5                   10                  15

Ser Ser Glu Ser Arg Pro Glu Val Val Ala Arg Leu Ile Ala Leu Leu
                20                  25                  30

Glu Glu Ala Ala Ser Gln Gly Ala Glu Leu Val Val Phe Pro Glu Leu
            35                  40                  45

Thr Leu Thr Thr Phe Phe Pro Arg Thr Trp Phe Glu Glu Gly Asp Phe
        50                  55                  60

Glu Glu Tyr Phe Asp Lys Ser Met Pro Asn Asp Asp Val Ala Pro Leu
65                  70                  75                  80

Phe Glu Arg Ala Lys Asp Leu Gly Val Gly Phe Tyr Leu Gly Tyr Ala
                85                  90                  95

Glu Leu Thr Ser Asp Glu Lys Arg Tyr Asn Thr Ser Ile Leu Val Asn
                100                 105                 110

Lys His Gly Asp Ile Val Gly Lys Tyr Arg Lys Met His Leu Pro Gly
            115                 120                 125

His Ala Asp Asn Arg Glu Gly Leu Pro Asn Gln His Leu Glu Lys Lys
        130                 135                 140

Tyr Phe Arg Glu Gly Asp Leu Gly Phe Gly Val Phe Asp Phe His Gly
145                 150                 155                 160

Val Gln Val Gly Met Cys Leu Cys Asn Asp Arg Arg Trp Pro Glu Val
                165                 170                 175

Tyr Arg Ser Leu Ala Leu Gln Gly Ala Glu Leu Val Leu Gly Tyr
                180                 185                 190

Asn Thr Pro Asp Phe Val Pro Gly Trp Gln Glu Pro His Ala Lys
            195                 200                 205

Met Phe Thr His Leu Leu Ser Leu Gln Ala Gly Ala Tyr Gln Asn Ser
        210                 215                 220

Val Phe Val Ala Ala Gly Lys Ser Gly Phe Glu Asp Gly His His
225                 230                 235                 240

Met Ile Gly Gly Ser Ala Val Ala Ala Pro Ser Gly Glu Ile Leu Ala
                245                 250                 255

Lys Ala Ala Gly Glu Gly Asp Glu Val Val Val Val Lys Ala Asp Ile
                260                 265                 270
```

Asp Met Gly Lys Pro Tyr Lys Glu Ser Val Phe Asp Phe Ala Ala His
            275                 280                 285

Arg Arg Pro Asp Ala Tyr Gly Ile Ile Ala Glu Arg Lys Gly Arg Gly
            290                 295                 300

Ala Pro Leu Pro Val Pro Phe Asn Val Asn Asp
305                 310                 315

<210> SEQ ID NO 3
<211> LENGTH: 26
<212> TYPE: DNA
<213> ORGANISM: ARTIFICIAL SEQUENCE
<220> FEATURE:
<223> OTHER INFORMATION: SYNTHETIC DNA

<400> SEQUENCE: 3
gatgttcacg caccttcttt cacttc                               26

<210> SEQ ID NO 4
<211> LENGTH: 25
<212> TYPE: DNA
<213> ORGANISM: ARTIFICIAL SEQUENCE
<220> FEATURE:
<223> OTHER INFORMATION: SYNTHETIC DNA

<400> SEQUENCE: 4
ggtgttgtag cccaggacga cgagc                                25

<210> SEQ ID NO 5
<211> LENGTH: 26
<212> TYPE: DNA
<213> ORGANISM: ARTIFICIAL SEQUENCE
<220> FEATURE:
<223> OTHER INFORMATION: SYNTHETIC DNA

<400> SEQUENCE: 5
gagggcgatg aagtcgtcgt tgtgaa                               26

<210> SEQ ID NO 6
<211> LENGTH: 25
<212> TYPE: DNA
<213> ORGANISM: ARTIFICIAL SEQUENCE
<220> FEATURE:
<223> OTHER INFORMATION: SYNTHETIC DNA

<400> SEQUENCE: 6
gttctggtat gcccctgcct gaagt                                25

<210> SEQ ID NO 7
<211> LENGTH: 26
<212> TYPE: DNA
<213> ORGANISM: ARTIFICIAL SEQUENCE
<220> FEATURE:
<223> OTHER INFORMATION: SYNTHETIC DNA

<400> SEQUENCE: 7
aacatatggc gaaaaacttg atgctc                               26

<210> SEQ ID NO 8
<211> LENGTH: 26
<212> TYPE: DNA
<213> ORGANISM: ARTIFICIAL SEQUENCE
<220> FEATURE:
<223> OTHER INFORMATION: SYNTHETIC DNA

<400> SEQUENCE: 8

```
aaggatccgt cattcacgtt gaacgg                                    26

<210> SEQ ID NO 9
<211> LENGTH: 29
<212> TYPE: DNA
<213> ORGANISM: ARTIFICIAL SEQUENCE
<220> FEATURE:
<223> OTHER INFORMATION: SYNTHETIC DNA

<400> SEQUENCE: 9
aaggatcctt agtcattcac gttgaacgg                                 29

<210> SEQ ID NO 10
<211> LENGTH: 17
<212> TYPE: DNA
<213> ORGANISM: ARTIFICIAL SEQUENCE
<220> FEATURE:
<223> OTHER INFORMATION: SYNTHETIC DNA
<220> FEATURE:
<221> NAME/KEY: misc_feature
<222> LOCATION: (3)..(3)
<223> OTHER INFORMATION: n = a, g, c, t

<400> SEQUENCE: 10
gtnatgtayg aracvgg                                              17

<210> SEQ ID NO 11
<211> LENGTH: 17
<212> TYPE: DNA
<213> ORGANISM: ARTIFICIAL SEQUENCE
<220> FEATURE:
<223> OTHER INFORMATION: SYNTHETIC DNA

<400> SEQUENCE: 11
gtrtartcca trttytc                                              17

<210> SEQ ID NO 12
<211> LENGTH: 13
<212> TYPE: PRT
<213> ORGANISM: ARTIFICIAL SEQUENCE
<220> FEATURE:
<223> OTHER INFORMATION: SYNTHETIC PEPTIDE

<400> SEQUENCE: 12

Ser Leu Val Met Tyr Glu Thr Gly Val Ala Glu Gly Lys
1               5                   10

<210> SEQ ID NO 13
<211> LENGTH: 11
<212> TYPE: PRT
<213> ORGANISM: ARTIFICIAL SEQUENCE
<220> FEATURE:
<223> OTHER INFORMATION: SYNTHETIC PEPTIDE

<400> SEQUENCE: 13

Gln Asn Met Asp Tyr Thr Leu Phe Glu Gly Lys
1               5                   10

<210> SEQ ID NO 14
<211> LENGTH: 8
<212> TYPE: PRT
<213> ORGANISM: ARTIFICIAL SEQUENCE
<220> FEATURE:
<223> OTHER INFORMATION: SYNTHETIC PEPTIDE
<220> FEATURE:
<221> NAME/KEY: MISC_FEATURE
<222> LOCATION: (2)..(2)
```

-continued

```
<223> OTHER INFORMATION: X = ANY AMINO ACID
<220> FEATURE:
<221> NAME/KEY: MISC_FEATURE
<222> LOCATION: (3)..(3)
<223> OTHER INFORMATION: X = ANY AMINO ACID
<220> FEATURE:
<221> NAME/KEY: MISC_FEATURE
<222> LOCATION: (5)..(5)
<223> OTHER INFORMATION: X = ANY AMINO ACID
<220> FEATURE:
<221> NAME/KEY: MISC_FEATURE
<222> LOCATION: (7)..(7)
<223> OTHER INFORMATION: X = ANY AMINO ACID

<400> SEQUENCE: 14

Gly Xaa Xaa Asp Xaa His Xaa His
1               5
```